(12) United States Patent
Bae et al.

(10) Patent No.: US 7,368,255 B2
(45) Date of Patent: May 6, 2008

(54) RUNX3 GENE SHOWING ANTI-TUMOR ACTIVITY AND USE THEREOF

(76) Inventors: Suk-Chul Bae, 107-302 Samik Apt., Gaesin-dong, Heungduck-ku, Chungcheongbuk-do (KR) 361-240; Yoshiaki Ito, 15-14 Higashidacho, Kamitakano, Sakyo-ku, Kyoto (JP) 606-0078

( * ) Notice: Subject to any disclaimer, the term of this patent is extended or adjusted under 35 U.S.C. 154(b) by 418 days.

(21) Appl. No.: 10/466,938

(22) PCT Filed: Jan. 30, 2001

(86) PCT No.: PCT/KR01/00121

§ 371 (c)(1),
(2), (4) Date: Jul. 18, 2003

(87) PCT Pub. No.: WO02/061069

PCT Pub. Date: Aug. 8, 2002

(65) Prior Publication Data

US 2004/0146986 A1  Jul. 29, 2004

(30) Foreign Application Priority Data

Jan. 29, 2001  (KR)  ........................ 2001-4018

(51) Int. Cl.
*G01N 33/574* (2006.01)
(52) U.S. Cl. .......................... 435/7.23; 435/6
(58) Field of Classification Search ................ None
See application file for complete search history.

(56) References Cited

OTHER PUBLICATIONS

Levanon et al, Oncogene 23:4211-4219, 2004.*
Kyeong-Sook Lee, et al., Runx2 Is a Common Target of Transforming Growth Factor β1 and Bone Morphogenetic Protein 2, and Cooperation between Runx2 and Smad5 Induces Osteoblast-Specific Gene Expression in the Pluripotent Mesenchymal Precursor Cell Line C2C12, Molecular and Cellular Biology, Dec. 2000, p. 8783-8792.

Scott C. Kogen, et al., The *PEBP2βMYH11* Fusion Created Inv(16)(p13;q22) in Myeloid Leukemia Impairs Neutrophil Maturation and Contributes to Granulocytic Dysplasia, Proc. Natl. Acad. Sci. USA vol. 95, pp. 11863-11868, Sep. 1998.

S-C. Bae, et al., Regulation Mechanisms for the Heterodimeric Transcription Factor, PEBP2/CBF, Histol Histopathol (1999) 14: 1213-1221.

Suk Chul Bae, et al., Isolation of *PEBP2 alphaβ* cDNA Representing the Mouse Homolog of Human Acute Myeloid Leukemia Gene, *AML1*, Oncogene (1993), 8, 809-814.

Mee-Young, Ahn, et al., Comparison of the Human Genomic Structure of the Runt Domain-Encoding PEBP2/CBF*alpha* Gene Family, Gene, 168 (1996) 279-280.

Amjad Javed, et al., Groucho/TLE/R-esp Proteins Associate with the Nuclear Matrix and Repress RUNX (CBF*alpha*/AML/PEBP2*alpha*) Dependent Activation of Tissue-Specific Gene Transcription, Journal of Cell Science 113, 2221-2231 (2000).

Yen-Yee Tang, et al., Energetic and Functional Contribution of Residues in the Core Binding Factor β (CBF β) Subunit to Heterodimerization with CBF*alpha*, The Journal of Biological Chemistry, vol. 275, No. 50, p. 39579-39588, 2000.

* cited by examiner

*Primary Examiner*—Misook Yu
*Assistant Examiner*—Mark Halvorson
(74) *Attorney, Agent, or Firm*—Lucas & Mercanti, LLP

(57) ABSTRACT

The present invention relates to a RUNX3 gene showing anti-tumor activity which is essentially involved in TGF-β dependent-programmed cell death (apoptosis) and use thereof. In addition, the present invention finds that the RUNX3 gene expression is suppressed in the various gastric cancer and lung cancer cell lines. The suppression of the RUNX3 gene expression is due to hyper-methylation of CpG island located around RUNX3 exon (1). The RUNX3 gene and its gene product of the present invention can be used effectively for the development of anti-cancer agents. CpG island around RUNX3 exon (1) could also be used not only for the development of anti-cancer agents which regulate the abnormal DNA methylation and there by induce RUNX3 expression but also for the development of methods for cancer diagnosis by measuring the abnormal DNA methylation.

7 Claims, 17 Drawing Sheets

FIG. 1a

```
CCGCCACTTGATTCTGGAGGATTTGTTCTGGGGCTGCGGCCGCGGAGTCG
        Ps-NA
GGGCGGCCGCGGGCGAGCTTCGGGGCGGGAGGCGGCGGCAGCGGCACAGC    100
CCCGCGCGGGCCCCGCCGCGGCCCAGGCAGCCGGGACAGCCACGAGGGGC
GGCCGCACGCGGGCCGCGCGCCGAGGATGCGGGACTAGCCGGGCAGGCT    200
GCGGGCGGCCGTCGGGCCAGCGAGGCCTCGCAGCGGGCGGGCCCTGGCGA
GTATTGGCCGGGCGCCGCCCCTGCGCCTGATGCCCGGGCCCCGCCGCT     300
TCTGCTTTCCCGCTTCTCGCGGCAGCGGCGGCCGAGGAGGCGCCCGCGCC
GGCCGCCCCGGGCGAAGCCGCGCCGTCTCCGCCTGCCCGGCGCCCTGAC    400
GGCCGCTGTTATGCGTATTCCCGTAGACCCAAGCACCAGCCGCCGCTTCA
CACCTCCCTCCCCGGCCTTCCCCTGCGGCGGCGGCGGCGGCAAGATGGGC    500
GAGAACAGCGGCCGCGCTGAGCGCGCAGGCGGCCGTGGGGCCCGGAGGGCG
CGCCCGGCCCGAGGTGCGCTCGATGGTGGACGTGCTGGCGGACCACGCAG    600
GCGAGCTCGTGCGCACCGACAGCCCCAACTTCCTCTGCTCCGTGCTGCCC
TCGCACTGGCGCTGCAACAAGACGCTGCCCGTCGCCTTCAAGGTGGTGGC    700
ATTGGGGGACGTGCCGGATGGTACGGTGGTGACTGTGATGGCAGGCAATG
ACGAGAACTACTCCGCTGAGCTGCGCAATGCCTCGGCCGTCATGAAGAAC    800
CAGGTGGCCAGGTTCAACGACCTTCGCTTCGTGGGCCGCAGTGGGCGAGG
GAAGAGTTTCACCCTGACCATCACTGTGTTCACCAACCCCACCCAAGTGG    900
        Ps-CA
CGACCTACCACCGAGCCATCAAGGTGACCGTGGACGGACCCCGGGAGCCC
AGACGGCACCGGCAGAAGCTGGAGGACCAGACCAAGCCGTTCCCTGACCG   1000
CTTTGGGGACCTGGAACGGCTGCGCATGCGGGTGACACCGAGCACACCCA
GCCCCGAGGCTCACTCAGCACCACAAGCCACTTCAGCAGCCAGCCCCAG    1100
           Ps-NB
ACCCCAATCCAAGGCACCTCGGAACTGAACCCATTCTCCGACCCCCGCCA
GTTTGACCGCTCCTTCCCCACGCTGCCAACCCTCACGGAGAGCCGCTTCC   1200
CAGACCCCAGGATGCATTATCCCGGGGCCATGTCAGCTGCCTTCCCCTAC
AGCGCCACGCCCTCGGGCACGAGCATCAGCAGCCTCAGCGTGGCGGGCAT   1300
GCCGGCCACCAGCCGCTTCCACCATACCTACCTCCCGCCACCCTACCCGG
GGGCCCCGCAGAACCAGAGCGGGCCCTTCCAGGCCAACCCGTCCCCCTAC   1400
CACCTCTACTACGGGACATCCTCTGGCTCCTACCAGTTCTCCATGGTGGC
CGGCAGCAGCAGTGGGGGCGACCGCTCACCTACCCGCATGCTGGCCTCTT   1500
GCACCAGCAGCGCTGCCTCTGTCGCCGCCGGCAACCTCATGAACCCCAGC
CTGGGCGGCCAGAGTGATGGCGTGGAGGCCGACGGCAGCCACAGCAACTC   1600
ACCCACGGCCCTGAGCACGCCAGGCCGCATGGATGAGGCCGTGTGGCGGC
CCTACTGACCGCCCTGGTGGACTCCTCCCGCTGGAGGCGGGGACCCTAAC   1700
                                            ◄
AACCTTCAAGACCAGTGATGGGCCGGCTCCGAGGCTCCGGGCGGGAATGG
   Ps-CB
GACCTGCGCTCCAGGGTGGTCTCGGTCCCAGGGTGGTCCCAGCTGGTGGG   1800
AGCCTCTGGCTGCATCTGTGCAGCCACATCCTTGTACAGAGGCATAGGTT
ACCACCCCACCCCGGCCCGGGATACTGCCCCCGGCCCAGATCCTGGCCG    1900
TCTCATCCCATACTTCTGTGGGCAATCAGCCTCCTGCCACCCCCCGGAA
GGACCTCACTGTCTCCAGCTATGCCCAGTGCTGCATGGGACCCATGTCTC   2000
CTGGGACAGAGGCCATCTCTCTTCCAGAGAGAGGCAGCATTGGCCCACAG
GATAAGCCTCAGGCCCTGGGAAACCTCCCGACCCCTGCACCTTCGTTGGA   2100
GCCCCTGCATCCCCTGGGTCCAGCCCCCTCTGCATTTACACAGATTTGAG
TCAGAACTGGAAAGTGTCCCCCACCCCCACCACCCTCGAGCGGGGTTCCC   2200
CTCATTGTACAGATGGGGCAGGACCCAGCACGCTGCTGGCAGAGATGGTT
TGAGAACACATCCAAGCCAGTCCCCCCAGCCCAGCTTCCCCTCCGTTCCT   2300
AACTGTTGGCTTTCCCCCAGCCGCACGGGTCCCAGGCCCCAGAGAAGATG
AGTCTATGGCATCAGGTTCTTAAACCCAGGAAAGCACCTACAGACCGGCT   2400
CCTCCATGCACTTTACCAGCTCAACGCATCCACTCTCTGTTCTCTTGGCA
GGGCGGGGAGGGGGATAGGAGGTCCCCTTTCCCCTAGGTGGTCTCATA    2500
ATTCCATTTGTGGAGAGAACAGGAGGGCCAGATAGATAGGTCCTAGCAGA
AGGCATTGAGGTGAGGGATCATTTTGGGTCAGACATCAATGTCCCTGTCC   2600
CCCCTGGGTCCAGCCAAGCTGTGCCCCATCCCCCAAGCCTCCTGGGAGGA
```

FIG. 1b

```
TCCAGCCAAATCTTGCGACTCCTGGCACACACCTGTCTGTAACCTGTTTT  2700
GTGCTCTGAAAGCAAATAGTCCTGAGCAAAAAAAAAAAAAAAACAAAAAA
ACAAAAAAAAAACAAAACAGTTTTTAAAACTGATTTTAGAAAAAGAAGCT  2800
TAATCTAACGTTTTCAAACACAAGGTCTCTTACAGGTATAGTTCCGTGAT
TATGATAGCTCTGTGATTATAAGCAACATCCCCGCCCCTCTCCCCCCCG  2900
CGGACCCCCAGCTGCCTCCTGAGGGTGTGGGGTTATTAGGGTCTCAATAC
TTTCTCAAGGGGCTACACTCCCCATCAGGCAGCATCCACCAGCCTGCAC  3000
CACAGGCTCCCCTGGGAGGACGAGGGAAACGCTGATGAGACGCTGGGCAT
CTCTCCTCTGTGGCTCTAGGACATCTGTCCAGGAGGCTGGGCGGAGGTGG  3100
GCAGGATGTGAGAGGTGGGGAGTACTGGCTGTGCGTGGCAGGACAGAAGC
ACTGTAAAGGGCTCTCCAGCCGCAGCTCAGCTGCACTGCGTTCCGAGGTG  3200
AAGTCTTGCCCCTGAATTTTGCAAAATGGGAAGTGGGCGCTTGCCCAAG
GGCCAGGCTGCATGGATTCTCACATCAGAGTTCTCTGGCCCTAGAAAGGC  3300
TTAGAAAAGGCGTAAGGGAACTCATAAAGGCTAGCAGCATGCGGTATTTT
AACTTTCTGCCTCGGCCTCTGTGGATGCAGAAATCTGCCCTACAAAATGC  3400
TCTTCATTGGTTGTCTCTGTGAGAGCACTGTCCCCACCCAACCTGTCACA
ACGGCCAGAACCATACACCAGAGACACACTGGCAGGTTAGGCAGTCCTTC  3500
TGGTGATCCTATTCCATTCCCTCCTGCTGCGGTTTCTCTTGGCCTGTCCT
CACTGGAAAAACAGTCTCCATCTCCTCAAAATAGTTGCTGACTCCCTGCA  3600
CCCAAGGGGCCTCTCCATGCCTTCTTAGGAAGCAGCTATGAATCCATTGT
CCTTGTAGTTTCTTCCCTCCTGTTCTCTGGTTATAGCTGGTCCCAGGTCA  3700
GCGTGGGAGGCACCTTTGGGTTCCCAGTGCCCAGCACTTTGTAGTCTCAT
CCCAGATTACTAACCCTTCCTGATCCTGGAGAGGCAGGGATAGTAAATAA  3800
ATTGCTCTTCCTACCCCATCCCCATCCCTGACAAAAAGTGACGGCAGC
CGTACTGAGTCTGTAAGGCCCAAAGTGGGTACAGACAGCCTGGGCTGGTA  3900
AAAGTAGGTCCTTATTTACAAGGCTGCGTTAAAGTTGTACTAGGCAAACA
CACTGATGTAGGAAGCACGAGGAAAGGAAGACGTTTTGATATAGTGTTAC  4000
TGTGAGCCTGTCAGTAGTGGGTACCAATCTTTTGTGACATATTGTCATGC
TGAGGTGTGACACCTGCTGCACTCATCTGATGTAAAACCATCCCAGAGCT  4100
GGCGAGAGGATGGAGCTGGGTGGAAACTGCTTTGCACTATCGTTTGCTTG
GTGTTTGTTTTTAACGCACAACTTGCTTGTACAGTAAACTGTCTTCTGTA  4200
CTATTTAACTGTA  3'
```

FIG. 1c

```
MRIPVDPSTSRRFTPPSPAFPCGGGGGKMGENSGALSAQAAVGPGGRARP
EVRSMVDVLADHAGELVRTDSPNFLCSVLPSHWRCNKTLPVAFKVVALGD
VPDGTVVTVMAGNDENYSAELRNASAVMKNQVARFNDLRFVGRSGRGKSF
TLTITVFTNPTQVATYHRAIKVTVDGPREPRRHRQKLEDQTKPFPDRFGD
LERLRMRVTPSTPSPRGSLSTTSHFSSQPQTPIQGTSELNPFSDPRQFDR
SFPTLPTLTESRFPDPRMHYPGAMSAAFPYSATPSGTSISSLSVAGMPAT
SRFHHTYLPPPYPGAPQNQSGPFQANPSPYHLYYGTSSGSYQFSMVAGSS
SGGDRSPTRMLASCTSSAASVAAGNLMNPSLGGQSDGVEADGSHSNSPTA
LSTPGRMDEAVWRPY
```

FIG. 2a

```
CCTTCTGCTTCCTAGCCCTGCTGTGGACAACTTAGGGTGCTCTTAGGTGG
GGGCCACTGGGGAGAAACTGGCCTGTTTGTCCATCGATCTGATGGAAGAG
GGAGAAAAGACGACGGTCCATGCCAACTGGGGAAGGGCGAGGGTGTCTGC
ATGCCCCAGGTGGGGGAGTCGGAGTTCTCCCTCCCATCAAACAGACGACA
ATTTTTGTCGGTCCGGGATGGGGAGGAAGCAGGTGGAAATTGGGAACAAG
CTAGCCTGTTCTGTGGGTGTTCCCCGGGTGCCTGAAAACGCGAAGACAGA
AGGCGTCCATCTTATCAGAGGTGAGGAAGGCGGCCTTGGTTTGACACAAA
GCCATCGGTTTGTCTGAGACCTGGCCGCATGGATGGCAAGGAAAGGGCAG
CTCCTCGGGGCGGTCGCCGCGCCTGCACCCGGGGCCGCAGCTGGCGCGC
ATCTGTAGCCCGGCCGGGCCCGCACCTCCGCGGCTGGCAGGGCGCGGGCG
CCAACTAGCGGCGGCTCCCGCCACTGTGCCTGCCAGGCGGCCCCGCGACC
TTGGTCTGGGGACCCAAGGGCCTGCACCCGCCCCCCTCCCCCGCCGCC
CTGGTCCCTTGGATCTGGTGCCCACGGGGAGCCAGCGCCCTACGGAGAGC
CGGAGCCGTGCCGGGCCCTGCGCCAGGTGCCAGGGCCCACAAGAGTCCCT
CATTCTCTGGAAACTTGTCTGTGAACCCATCGTAAGCGGAGAGGGAGAAA
TCAGGCGGAGGAACAAGCAAAGGGCACGGTGCAAACCGAAACCATTCGAC
AAATGGAATTTACCACCACCTGAAACAGCGGGTCATGGTCCCGCAACCTG
CTCGAGGGCAGCACGTGTTGCCCGCCCCGGCCAGGGCCCTACCTGGCCA
CGACGCGCTGCGCCTTCTCGGAGACGTTCCCGGAGGTGGGAGCGCCCAGG
CTGGATCACTCGCTTTCCTCTAGTTCTGCTGCTCGTGCCAGCGCGTCCGA
GGGCGCGCGGGCCTGGGTCCGCAATCGACAACTGCCAGGCGCAGGCTCTC
TTAAAAGGTTCAGTAAGGGACCTTTGCCGTCCTTCCTTTCGACACGGCCT
GAGGGCGTGCTGTGAGGTCCCGAGGTGGGTAGGGGCCAGCTCTCCCGGTG
GTCGGGGTGAGTCCAGAGTCCTTCGCCCCTGGAGCGCACGCGGGGCTTGA
TTTCGTTTGGCAACGACGAAATGGCGCGCGCTGAGCAGGGGTCAGATCCA
TGATGAGATCTTGCGGCCACCGTCGGATCCTAAGCTTCTTTGCTTCCGAG
GCTTGGAATTCATTGTTTGCACCTGTCGAGAGCCGGAGGCAACGAAAAT
CTAGCCCCGTCTCCAAAGCGGCGGGGAGGCTCAGCACGCGTTCGTTCCCC
AGAGTCTAGGGAGGTGTCTGGGGCGATAATTCGGAATGATTGTGGCTTGA
TCTTTCCCGTTGCCCTCCCAACTGTAGCCGGCCCCTAGGTCTGCTCGACA
GACTTAGGAGGCGGGAGAGGAAGGGGTGATTTGCAGTGAAGCCCAGGAGA
GGTTGGGCCACGCGGCTGGGAGTGGGAGCGGGGACCCGGAGCCGGGCGGG
CAGGCAGTGCCTTGGCGAAGCTGTCCGCGGTCCCTGCGGCGCAGCCGGAG
CGCACGGGCCCAAGAAGAAGTGGGGTTGGACCCGCAGAGGCCACTTTCCA
CCCGCATGGAGAAAGAAAATTCTCTCCTCTGAAAGCGAGGGCCCTTAGCT
TTGCAGCCACTGCTGTTTTCTTTTGCCACCGACGCGCGTACCGTTTCAC
GATGCAGGACCGTGGTTACATGCGTAAAGGAAAAAAAGAAAAACGCATTT
TGCAGGCCTCGTCGTGTTTTTCAAAGAGCCACAGGCCGCTACAACGAAGA
```

FIG. 2b

ACGACGCCGCGAGGCCTGCAAGATCCTGAAACTTGTTTTGAGGGGAGAGC
AGAGAGGAAAGGGGTTGTTGGCCCCAGGCTACTTAGGGTCCCTAGGAGAC
TCCCTTCCGCCTGTCCCCGGTTTGGCACAGGGGCCACCGAGGCTGGGACC
AAAGCCGCGCAGGGCTGGGAGCAGCAAAGGCCGCCGGCCGGGCGTGGACG
ACGCGCAAAATCCCGTGTGGGGTGGAGGCTCTTGGGTCAGAATAATGTGC
GGGACGAGGGAGGTGAGTAACCTCTTTGGGGCGGCTCCCAGTGCGGCGTC
ACCGGCCCTGAGACCCCGCGGCCCCAGCCCGGGGTTGCAGAAGTCACAG
GCCCGAAGCAGCAAGAGCTGGGGAAGCCCGGCCGCGGCCAGCGGGGAGGA
GGAGCGAAGGGGTTGCGCCCAGCGTCAGGGAGCTACGACCCGAGAGAGG
GCGGCAAGGGCGCCTTCCGTGGGACCCGGACGTTCTAAGCAAATTTCTAG
CATTTGCCCCGGGCTCCCAGAGCTCTCGGGGGCCCTGGGCTGTGGCACTG
GGGCCTCCTCCGCGGGGTGGCGCCTTCCGCCCCTCCCCGTTGGGCGGCCT
CCGGCAGGCCCCGTTCCTCCCGCGAACGCCACCGAGGTGCCCGCGATGG
GGGCTCCGCCGATTGGCTGTGCGACGCGTCGCTCCGCCAGCCCCGCCCCG
CGGGCCCCGGGGGTACTAACCCCGCGCGGGCGGCCGCGGCCCCGCCACTT
GATTCTGGAGGATTTGTTCTGGGGCTGCGGCCGCGGAGTCGGGGCGGCCG
CGGGCGAGCTTCGGGGCGGGAGGCGGCGGCAGCGGCACAGCCCCGCGCGG
GCCCCGCCGCGGCCCAGGCAGCCGGGACAGCCACGAGGGGCGGCCGCACG
CGGGGCCGCGCGCCGAGGATGCGGGACTAGCCGGGCAGGCTGCGGGCGGC
CGTCGGGCCAGCGAGGCCTCGCAGCGGGCGGGCCTGGCGAGTAGTGGCC
GGGCGCCGCCCCTGCGCCTGAGGCCCGGGCCCCGCCGCTTCTGCTTTC
CCGCTTCTCGCGGCAGCGGCGGCCGAGGAGGCGCCCGCGCCGGCCGCCCC
CGGGGGAAGCCGCGCCGTCTCCGCCTGCCCGGCGCCCTGACGGCCGCTGT
TATGCGTATTCCCGTAGACCCAAGCACCAGCCGCCGCTTCACACCTCCCT
CCCCGGCCTTCCCCTGCGGCGGCGGCGGCAAGATGGGCGAGAACAGC
GGCGCCCTGAGCGCGCAGGCGCCGTGGGGCCCGGAGGGCGCGCCCGGCC
CGAGGTGCGCTCGATGGTGGACGTGCTGGCGGACCACGCAGGCGAGCTCG
TGCGCACCGACAGCCCCAACTTCCTCTGCTCCGTGCTGCCCTCGCACTGG

FIG. 5c
MKN28
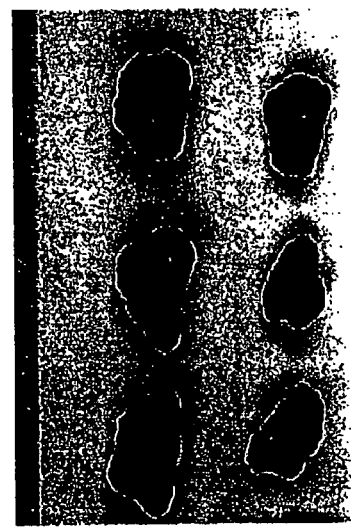
MKN28-Rx3
SNU16
SNU16-Rx3-AS-cl1
SNU16-Rx3-AS-cl2 o: SmaI  ●: HaeII  ▲: BamHI  □: MluI  ◆: NheI

SEQUENCE LISTING

```
<160> NUMBER OF SEQ ID NOS: 11

<210> SEQ ID NO 1
<211> LENGTH: 4213
<212> TYPE: DNA
<213> ORGANISM: human SNUX3 cDNA gene

<400> SEQUENCE: 1
ccgccacttg attctggagg atttgttctg gggctgcggc cgcggagtcg gggcggccgc      60
gggcgagctt cggggcggga ggcggcggca gcggcacagc cccgcgcggg ccccgccgcg     120
gcccaggcag ccgggacagc cacgaggggc ggccgcacgc ggggccgcgc gccgaggatg     180
cgggactagc cgggcaggct gcgggcggcc gtcgggccag cgaggcctcg cagcgggcgg     240
gccctggcga gtattggccg ggcgccgccc cctgcgccct gatgcccggg ccccgccgct     300
tctgctttcc cgcttctcgc ggcagcggcg gccgaggagg cgcccgcgcc ggccgccccc     360
gggggaagcc gcgccgtctc cgcctgcccg gcgccctgac ggccgctgtt atgcgtattc     420
ccgtagaccc aagcaccagc cgccgcttca cacctccctc cccggccttc ccctgcggcg     480
gcggcggcgg caagatgggc gagaacagcg gcgcgctgag cgcgcaggcg gccgtggggc     540
ccggagggcg cgcccggccc gaggtgcgct cgatggtgga cgtgctggcg gaccacgcag     600
gcgagctcgt gcgcaccgac agccccaact tcctctgctc cgtgctgccc tcgcactggc     660
gctgcaacaa gacgctgccc gtcgccttca aggtggtggc attgggggac gtgccggatg     720
gtacggtggt gactgtgatg gcaggcaatg acgagaacta ctccgctgag ctgcgcaatg     780
cctcggccgt catgaagaac caggtggcca ggttcaacga ccttcgcttc gtgggccgca     840
gtgggcgagg gaagagtttc acctgacca tcactgtgtt caccaacccc acccaagtgg     900
cgacctacca ccgagccatc aaggtgaccg tggacggacc ccgggagccc agacggcacc     960
ggcagaagct ggaggaccag accaagccgt tccctgaccg ctttgggggac ctggaacggc    1020 tgcgcatgcg ggtgacaccg agcacaccca gcccccgagg ctcactcagc accacaagcc    1080
```

```
acttcagcag ccagcccag accccaatcc aaggcacctc ggaactgaac ccattctccg    1140
accccgcca gtttgaccgc tccttcccca cgctgccaac cctcacggag agccgcttcc    1200
cagaccccag gatgcattat cccgggccca tgtcagctgc cttccctac agcgccacgc    1260
cctcgggcac gagcatcagc agcctcagcg tggcgggcat gccggccacc agccgcttcc    1320
accataccta cctcccgcca ccctacccgg ggccccgca gaaccagagc gggcccttcc    1380
aggccaaccc gtcccctac cacctctact acgggacatc tctggctcc taccagttct    1440
ccatggtggc cggcagcagc agtgggggcg accgctcacc tacccgcatg ctggcctctt    1500
gcaccagcag cgctgcctct gtcgccgccg gcaacctcat gaaccccagc ctgggcggcc    1560
agagtgatgg cgtggaggcc gacggcagcc acagcaactc acccacggcc ctgagcacgc    1620
caggccgcat ggatgaggcc gtgtggcggc cctactgacc gccctggtgg actcctcccg    1680
ctggaggcgg ggaccctaac aaccttcaag accagtgatg ggccggctcc gaggctccgg    1740
gcgggaatgg gacctgcgct ccagggtggt ctcggtccca gggtggtccc agctggtggg    1800
agcctctggc tgcatctgtg cagccacatc cttgtacaga ggcataggtt accaccccca    1860
ccccggcccg ggatactgcc cccggcccag atcctggccg tctcatccca tacttctgtg    1920
gggaatcagc ctcctgccac ccccccggaa ggacctcact gtctccagct atgcccagtg    1980
ctgcatggga cccatgtctc ctgggacaga ggccatctct cttccagaga gaggcagcat    2040
tggcccacag gataagcctc aggccctggg aaacctcccg accctgcac cttcgttgga    2100
gccctgcat cccctgggtc cagccccctc tgcatttaca cagatttgag tcagaactgg    2160
aaagtgtccc ccacccccac caccctcgag cggggttccc ctcattgtac agatggggca    2220
ggacccagca cgctgctggc agagatggtt tgagaacaca tccaagccag tcccccagc    2280
ccagcttccc ctccgttcct aactgttggc tttcccccag ccgcacgggt cccaggcccc    2340
agagaagatg agtctatggc atcaggttct taaacccagg aaagcaccta cagaccggct    2400
cctccatgca ctttaccagc tcaacgcatc cactctctgt tctcttggca gggcggggga    2460
gggggatag gaggtcccct ttcccctagg tggtctcata attccatttg tggagagaac    2520
aggagggcca gatagatagg tcctagcaga aggcattgag gtgagggatc attttgggtc    2580
agacatcaat gtccctgtcc ccctgggtc cagccaagct gtgccccatc ccccaagcct    2640
cctgggagga tccagccaaa tcttgcgact cctggcacac acctgtctgt aacctgtttt    2700
gtgctctgaa agcaaatagt cctgagcaaa aaaaaaaaa aaacaaaaaa acaaaaaaaa    2760
aacaaaacag tttttaaaac tgattttaga aaaagaagct taatctaacg ttttcaaaca    2820
caaggtctct tacaggtata gttccgtgat tatgatagct ctgtgattat aagcaacatc    2880
cccgcccct ctccccccg cggaccccca gctgcctcct gagggtgtgg ggttattagg    2940
gtctcaatac tttctcaagg ggctacactc cccatcaggc agcatccac cagcctgcac    3000
cacaggctcc cctgggagga cgagggaaac gctgatgaga cgctgggcat ctctcctctg    3060
tggctctagg acatctgtcc aggaggctgg gcggaggtgg gcaggatgtg agaggtgggg    3120
agtactggct gtgcgtggca ggacagaagc actgtaaagg gctctccagc cgcagctcag    3180
ctgcactgcg ttccgaggtg aagtcttgcc cctgaatttt gcaaaatggg aaagtgggcg    3240
cttgcccaag ggccaggctg catggattct cacatcagag ttctctggcc ctagaaaggc    3300
ttagaaaagg cgtaagggaa ctcataaagg ctagcagcat gcggtatttt aactttctgc    3360
ctcggcctct gtggatgcag aaatctgccc tacaaaatgc tcttcattgg ttgtctctgt    3420
gagagcactg tccccaccca acctgtcaca acggccagaa ccatacacca gagacacact    3480
```

```
ggcaggttag gcagtccttc tggtgatcct attccattcc ctcctgctgc ggtttctctt   3540
ggcctgtcct cactggaaaa acagtctcca tctcctcaaa atagttgctg actccctgca   3600 cccaagggc  ctctccatgc cttcttagga agcagctatg aatccattgt ccttgtagtt   3660
tcttccctcc tgttctctgg ttatagctgg tcccaggtca gcgtgggagg cacctttggg   3720
ttcccagtgc ccagcacttt gtagtctcat cccagattac taaccccttcc tgatcctgga  3780 gaggcaggga tagtaaataa attgctcttc ctaccccatc cccatcccc  tgacaaaaag   3840 tgacggcagc cgtactgagt ctgtaaggcc caaagtgggt acagacagcc tgggctggta   3900
aaagtaggtc cttatttaca aggctgcgtt aaagttgtac taggcaaaca cactgatgta   3960
ggaagcacga ggaaaggaag acgttttgat atagtgttac tgtgagcctg tcagtagtgg   4020
gtaccaatct tttgtgacat attgtcatgc tgaggtgtga cacctgctgc actcatctga   4080
tgtaaaacca tcccagagct ggcgagagga tggagctggg tggaaactgc tttgcactat   4140
cgtttgcttg gtgtttgttt ttaacgcaca acttgcttgt acagtaaact gtcttctgta   4200
ctatttaact gta                                                     4213
```

<210> SEQ ID NO 2
<211> LENGTH: 415
<212> TYPE: PRT
<213> ORGANISM: human SNUX3 protein

<400> SEQUENCE: 2

```
Met Arg Ile Pro Val Asp Pro Ser Thr Ser Arg Phe Thr Pro Pro
 1               5                  10                  15

Ser Pro Ala Phe Pro Cys Gly Gly Gly Gly Lys Met Gly Glu Asn
                20                  25                  30

Ser Gly Ala Leu Ser Ala Gln Ala Val Gly Pro Gly Gly Arg Ala
            35                  40                  45

Arg Pro Glu Val Arg Ser Met Val Asp Val Leu Ala Asp His Ala Gly
     50                  55                  60

Glu Leu Val Arg Thr Asp Ser Pro Asn Phe Leu Cys Ser Val Leu Pro
 65                  70                  75                  80

Ser His Trp Arg Cys Asn Lys Thr Leu Pro Val Ala Phe Lys Val Val
                 85                  90                  95

Ala Leu Gly Asp Val Pro Asp Gly Thr Val Val Thr Val Met Ala Gly
                100                 105                 110

Asn Asp Glu Asn Tyr Ser Ala Glu Leu Arg Asn Ala Ser Ala Val Met
            115                 120                 125

Lys Asn Gln Val Ala Arg Phe Asn Asp Leu Arg Phe Val Gly Arg Ser
130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
                165                 170                 175

Pro Arg Glu Pro Arg Arg His Arg Gln Lys Leu Glu Asp Gln Thr Lys
            180                 185                 190

Pro Phe Pro Asp Arg Phe Gly Asp Leu Glu Arg Leu Arg Met Arg Val
        195                 200                 205

Thr Pro Ser Thr Pro Ser Pro Arg Gly Ser Leu Ser Thr Thr Ser His
    210                 215                 220

Phe Ser Ser Gln Pro Gln Thr Pro Ile Gln Gly Thr Ser Glu Leu Asn
225                 230                 235                 240
```

-continued

```
Pro Phe Ser Asp Pro Arg Gln Phe Asp Arg Ser Phe Pro Thr Leu Pro
                245                 250                 255
Thr Leu Thr Glu Ser Arg Phe Pro Asp Pro Arg Met His Tyr Pro Gly
            260                 265                 270
Ala Met Ser Ala Ala Phe Pro Tyr Ser Ala Thr Pro Ser Gly Thr Ser
        275                 280                 285
Ile Ser Ser Leu Ser Val Ala Gly Met Pro Ala Thr Ser Arg Phe His
    290                 295                 300
His Thr Tyr Leu Pro Pro Pro Tyr Pro Gly Ala Pro Gln Asn Gln Ser
305                 310                 315                 320
Gly Pro Phe Gln Ala Asn Pro Ser Pro Tyr His Leu Tyr Tyr Gly Thr
                325                 330                 335
Ser Ser Gly Ser Tyr Gln Phe Ser Met Val Ala Gly Ser Ser Ser Gly
            340                 345                 350
Gly Asp Arg Ser Pro Thr Arg Met Leu Ala Ser Cys Thr Ser Ser Ala
        355                 360                 365
Ala Ser Val Ala Ala Gly Asn Leu Met Asn Pro Ser Leu Gly Gly Gln
    370                 375                 380
Ser Asp Gly Val Glu Ala Asp Gly Ser His Ser Asn Ser Pro Thr Ala
385                 390                 395                 400
Leu Ser Thr Pro Gly Arg Met Asp Glu Ala Val Trp Arg Pro Tyr
                405                 410                 415

<210> SEQ ID NO 3
<211> LENGTH: 3300
<212> TYPE: DNA
<213> ORGANISM: CpG island in EXON 1 of human RUNX3 gene

<400> SEQUENCE: 3
ccttctgctt cctagccctg ctgtggacaa cttagggtgc tcttaggtgg gggccactgg      60
ggagaaactg gcctgtttgt ccatcgatct gatggaagag ggagaaaaga cgacggtcca     120
tgccaactgg ggaagggcga gggtgtctgc atgccccagg tggggagtc ggagttctcc      180 ctcccatcaa acagacgaca atttttgtcg gtccgggatg gggaggaagc aggtggaaat     240
tgggaacaag ctagcctgtt ctgtgggtct tccccgggtg cctgaaaacg cgaagacaga     300
aggcgtccat cttatcagag gtgaggaagg cggccttggt ttgacacaaa gccatcggtt     360
tgtctgagac ctggccgcat ggatggcaag gaaagggcag ctcctcgggg gcggtcgccg     420
cgcctgcacc cggggccgca gctggcgcgc atctgtagcc cggccgggcc cgcacctccg     480
cggctggcag ggcgcgggcg ccaactagcg gcggctcccg ccactgtgcc tgccaggcgg     540
ccccgcgacc ttggtctggg gacccaaggg cctgcacccg ccccccctcc cccgccgcc      600 ctggtccctt ggatctggtg cccacgggga gccagcgccc tacggagagc cggagccgtg     660
ccgggccctc gccaggtgc cagggcccac aagagtccct cattctctgg aaacttgtct      720
gtgaacccat cgtaagcgga gagggagaaa tcaggcggag gaacaagcaa agggcacggt     780
gcaaaccgaa accattcgac aaatggaatt taccaccacc tgaaacagcg ggtcatggtc     840
ccgcaacctg ctcgagggca gcacgtgttg cccgccccg gccagggccc tacctggcca      900
cgacgcgctg cgccttctcg gagacgttcc cggaggtggg agcgcccagg ctggatcact     960
cgctttcctc tagttctgct gctcgtgcca gcgcgtccga gggcgcgcgg gcctgggtcc    1020
gcaatcgaca actgccaggc gcaggctctc ttaaaaggtt cagtaaggga cctttgccgt    1080
ccttcctttc gacacggcct gagggcgtgc tgtgaggtcc cgaggtgggt aggggccagc    1140
```

```
tctcccggtg gtcggggtga gtccagagtc cttcgcccct ggagcgcacg cggggcttga    1200
tttcgtttgg caacgacgaa atggcgcgcg ctgagcaggg gtcagatcca tgatgagatc    1260
ttgcggccac cgtcggatcc taagcttctt tgcttccgag gcttggaatt cattgttttg    1320
cacctgtcga gagccggagg caacgaaaat ctagccccgt ctccaaagcg gcggggaggc    1380
tcagcacgcg ttcgttcccc agagtctagg gaggtgtctg gggcgataat tcggaatgat    1440
tgtggcttga tctttcccgt tgccctccca actgtagccg gcccctaggt ctgctcgaca    1500
gacttaggag gcgggagagg aaggggtgat ttgcagtgaa gccaggagag ggttgggcca    1560
cgcggctggg agtgggagcg gggacccgga gccgggcggg caggcagtgc cttggcgaag    1620
ctgtccgcgg tccctgcggc gcagccgagg cgcacgggcc caagaagaag tggggttgga    1680
cccgcagagg ccactttcca cccgcatgga gaaagaaaat tctctcctct gaaagcgagg    1740
gcccttagct ttgcagccac tgctgttttt cttttgccac cgacgcgcgt accgtttcac    1800
gatgcaggac cgtggttaca tgcgtaaagg aaaaaaagaa aaacgcattt tgcaggcctc    1860
gtcgtgtttt tcaaagagcc acaggccgcc acaacgaaga acgacgccgc gaggcctgca    1920
agatcctgaa acttgttttg aggggagagc agagaggaaa ggggttgttg gccccaggct    1980
acttagggtc cctaggagac tcccttccgc ctgtccccgg tttggcacag gggccaccga    2040
ggctgggacc aaagccgcgc agggctggga gcagcaaagg ccgccggccg ggcgtggacg    2100
acgcgcaaaa tcccgtgtgg ggtggaggct cttgggtcag aataatgtgc gggacgaggg    2160
aggtgagtaa cctcttgggg gcggctccca gtgcggcgtc accggccctg agaccccgcg    2220
gcccccagcc cggggttgca gaagtcacag gcccgaagca gcaagagctg gggaagcccg    2280
gccgcggcca gcggggagga ggagcgaagg ggttgcgccc cagcgtcagg gagctacgac    2340
ccgagagagg gcggcaaggg cgccttccgt gggacccgga cgttctaagc aaatttctag    2400
catttgcccc gggctcccag agctctcggg ggccctgggc tgtggcactg gggcctcctc    2460
cgcggggtgg cgccttccgc ccctccccgt tgggcggcct ccggcaggcc ccgttcctcc    2520
ccgcgaacgc caccgaggtg cccgcgatgg gggctccgcc gattggctgt gcgacgcgtc    2580
gctccgccag ccccgccccg cgggccccgg gggtactaac cccgcgcggg cggccgcggc    2640
cccgccactt gattctggag gatttgttct ggggctgcgg ccgcggagtc ggggcggccg    2700
cgggcgagct tcggggcggg aggcggcggc agcggcacag cccgcgcgg ggccccgccgc    2760 ggcccaggca gccgggacag ccacgagggg cggccgcacg cggggccgcg cgccgaggat    2820
gcgggactag ccgggcaggc tgcgggcggc cgtcgggcca gcgaggcctc gcagcgggcg    2880 ggccctgggcg agtagtggcc gggcgccgcc cctgcgccc tgaggcccgg gccccgccgc    2940
ttctgctttc ccgcttctcg cggcagcggc ggccgaggag gcgcccgcgc cggccgcccc    3000
cgggggaagc cgcgccgtct ccgcctgccc ggcgccctga cggccgctgt tatgcgtatt    3060
cccgtagacc caagcaccag ccgccgcttc acacctccct cccccggcctt ccctgcggc    3120 ggcggcggcg gcaagatggg cgagaacagc ggcgcgctga gcgcgcaggc ggccgtgggg    3180
cccggagggc gcgcccggcc cgaggtgcgc tcgatggtgg acgtgctggc ggaccacgca    3240
ggcgagctcg tgcgcaccga cagccccaac ttcctctgct ccgtgctgcc ctcgcactgg    3300
                                                                    3300
```

<210> SEQ ID NO 4
<211> LENGTH: 25
<212> TYPE: DNA
<213> ORGANISM: Artificial Sequence
<220> FEATURE:

<223> OTHER INFORMATION: Description of Artificial Sequence: sense
      primer of Ps-N primer pair

<400> SEQUENCE: 4
cgccacttga ttctggagga tttgt                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: antisense
      primer of Ps-N primer pair

<400> SEQUENCE: 5
tgaagtggct tgtggtgctg agtga                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: sense
      primer of Ps-C primer pair

<400> SEQUENCE: 6
gagtttcacc ctgaccatca ctgtg                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: antisense
      primer of Ps-C primer pair

<400> SEQUENCE: 7
gcccatcact ggtcttgaag gttgt                                              25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: sense
      primer of PEBP2 beta/CBFB cDNA primer pair

<400> SEQUENCE: 8
cacgcttcca gaacgcctgc                                                    20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: antisense
      primer of PEBP2 beta/CBFB cDNA primer pair

<400> SEQUENCE: 9
cgagcctctt caaaggcctg t                                                  21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: sense -continued primer of beta-actin primer pair
<400> SEQUENCE: 10
ggacttcgag caagagatgg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: antisense
      primer beta-actin cDNA primer pair

<400> SEQUENCE: 11
gtcaccttca ccgttccagt                                              20

RUNX3 GENE SHOWING ANTI-TUMOR ACTIVITY AND USE THEREOF

This patent application claims a benefit of priority from Korean Patent Application No. 2001-4018 filed Jan. 29, 2001 through PCT Application Ser. No. PCT/KR01/00121 filed Jan. 30, 2001, the contents of each of which are incorporated herein by reference.

FIELD OF THE INVENTION

The present invention relates to the RUNX3 gene and uses thereof as an anticancer agent. More specifically, the present invention relates to characterization of the RUNX3 gene, its expression and tumor suppressor activity, and its use in the development of cancer diagnosis methods and anticancer agents.

BACKGROUND OF THE INVENTION

Tumors are assemblies of cells that show excessive autonomous proliferation, and are classified into malignant tumors, which may result in death, and benign tumors; however, it can be difficult to discriminate between these types. Cancers are genetic diseases attributed to the mutation of genes such as oncogenes and tumor suppressor genes, and their causes can be found at a cellular level. Oncogene products constitute a signaling network within cells, and are involved in regulating signal transduction systems for cell division and differentiation. When their regulation becomes abnormal, cells do not differentiate further, but rather divide infinitely; that is, they become tumorigenic. If a way could be found to enable such an abnormal signal transduction pathway to be converted into a normal one, anticancer agents could be developed that would obtain excellent therapeutic effects without side effects.

At present, cancers are for the most part treated in three ways: with surgical therapy, chemical therapy, and radiation therapy. In practice, combinations of these therapies or further combination with laser therapy are prevalent. However, chemical therapy is preferred to other therapies when the pain accompanying therapy and metastatic conditions are taken into account. Numerous anticancer agents have been developed, most of which are based on the selective killing of cells that are actively dividing. However, these anticancer agents suffer from the disadvantage of also killing some normal cells, such as immune cells and hair root cells, with concomitant significant side effects; they are thus not able to be used for long periods of time. Therefore, there remains a need for novel anticancer agents. A therapeutic agent based on the causes of cancer might be expected to be highly effective and to have few or no accompanying side effects.

Abnormal activation of oncogenes induces cell proliferation, and is one cause of cancer. In contrast, tumor suppressor genes function to prevent abnormal cell proliferation or to trigger programmed cell death (apoptosis). Often, tumor suppressor genes trigger apoptosis to kill the cells with abnormally activated oncogenes thus preventing the formation of cancerous cells. Where tumor suppressor genes show normal activity, cells with abnormally activated oncogenes cannot progress toward cancer, but are annihilated. Therefore, to become cancerous cells, cells must have inactivated tumor suppressor genes as well as activated oncogenes.

One of the mechanisms by which tumor suppressor genes are inactivated is by hyper-methylation of CpG islands (Jones and Laird, Nature Genet. Vol. 21, 163-167, 1999).

Methylation of CpG islands is performed by DNA methyltransferase. After significant methylation, DNA binding proteins such as methyl cytosine binding protein 2 (MECP2) bind to the methylated cytosine of the DNA, which recruits histone deacetylase (HDAC) to repress gene expression. In detail, HDAC removes the acetyl groups associated with histones, and the chromosomal DNA in the vicinity of the deacetylated histones becomes dense, which leads to repression of gene transcription. If gene expression is repressed by DNA methylation, DNA methyltransferase or HDAC inhibitors may be useful for inducing gene expression. Tumor suppressor genes whose expression is repressed by DNA methylation are exemplified by RB1, TP53, VHL, CDKN2A, CDKN2B, MLH1, and APC (Jones and Laird, Nature Genet. Vol. 21, 163-167, 1999).

As mentioned previously, histone acetylation and deacetylation are known to play important roles in regulating DNA transcription in eukaryotic cells (Grunstein M., Nature, 389, 349-352, 1997). Some naturally occurring compounds have been found to prevent cells from progressing toward cancer by inhibiting HDAC. Exemplified by trapoxin, trichostatin A, and depudecin, HDAC inhibitors have been studied for their ability to reverse the transformation of cancerous cells. Of the HDAC inhibitors, depudecin is the best characterized as to its anti-angiogenic activity in vivo and in vitro. In addition, the HDAC inhibitors have been studied with regard to cellular responses, including cell cycle interruption, alteration of gene expression patterns, and induction of apoptosis.

The TGF-β signal transduction system is well known for its tumor suppressor activity. The binding of TGF-β to TGF-β receptors causes the activation of the receptors, which in turn activate Smad proteins by phosphorylation. Once activated, Smad proteins move into the nucleus and regulate gene expression in cooperation with other transcription factors, thereby suppressing cell division or inducing apoptosis (Massague et al., Cell, 103 (2):295-309, 2000). Runx3 is one of the transcription factors that physically interact with Smad proteins (Hanai et al., J. Biol. Chem. 274; 31577-31582, 1999). Deletion or mutation of TGF-β receptors or Smad genes is observed in cells of various types of cancer. The tumor suppressor activity of TGF-β receptors was also demonstrated by an experiment in a cell strain lacking the TGF-β receptor. When the cell was transformed to express the TGF-β receptor, cell proliferation was reduced and tumorigenesis was decreased in an assay in nude mice (Chang et al., Cancer Res., 57 (14):2856-2859, 1997). The TGF-β signal transduction system is well characterized as to the repression of cell proliferation, which is achieved by promoting the expression of the CDK inhibitor protein p21. However, the mechanism by which TGF-β induces apoptosis remains to be clearly elucidated.

PEBP2 (polyoma virus enhancer binding protein 2) is composed of two submits, α and β. There are three genes which encode the α subunit.: RUNX1/PEBP2α B/CBFA2/AML1, RUNX2/PEBP2α A/CBFA2/AML2, and RUNX3/PEBP2α C/CBFA3/AML2 (Bae and Ito, Histol. Histopathol, 14(4):1213-1221, 1999). The RUNX1, RUNX2, and RUNX3 genes show homology of about 60-70% in amino acid sequence among them. They are highly conserved evolutionarily, with homology of about 95% between mouse and human.

Regarded as an important causative gene in leukemia, the RUNX1 gene becomes associated with other genes by chromosome translocation to cause acute myeloid leukemia or acute lymphoid leukemia in humans (Miyoshi et al., EMBO J., 12:2715-2721, 1993; Romana et al., Blood, 85:3662-3670, 1995; Okuda et al., Blood, 91:3134-3143, 1998; Okuda et al., Cell, 84:321-330, 1996). The RUNX2 gene plays a crucial role in osteogenesis, and its disruption has been implicated in causing cleidocranial dysplasia (Komori et al., Cell, 89:755-764, 1997; Lee et al., Nat. Genet., 15:307-310, 1997; Mundlos et al., Cell, 89:773-779, 1997; Otto et al., Cell, 89:756-771, 1997). Also, it has been reported that the RUNX2 gene shows oncogenic activity in the formation of T-cell lymphoma (Stewart et al., Proc. Natl. Acad. Sci. U.S.A., 94(16):8646-8651, 1997).

The RUNX3 gene was identified by the present inventors several years ago as a member of the PEBP2 family (Bae et al., Gene, 159(2):245-248, 1995; Levanon et al., Genomics, 23(2):425-532, 1994). However, diseases associated with the activation or inactivation of the RUNX3 gene, other than what we describe in this invention, hasn't been reported.

SUMMARY OF THE INVENTION

Leading to the present invention, the thorough and intensive research on diseases associated with the activation of the RUNX3 gene, conducted by the present inventors, resulted in the finding that RUNX3 gene products have tumor suppressor activity. RUNX3 is indispensable for TGF-β-induced apoptosis, and inactivation of the RUNX3 gene by DNA methylation at loci near RUNX3 exon 1 is closely correlated with cancer development. In the present invention, the RUNX3 gene is characterized as to its expression and tumor suppressor activity, offering the possibility of developing cancer diagnosis methods and anticancer agents from it.

The objectives of the present invention are to elucidate the tumor suppressor activity of the RUNX3 gene and its mechanism, and to provide a diagnostic method and a therapeutic agent for cancer based on the tumor suppressor activity of RUNX3.

To achieve the above objectives, the present invention provides a cell strain having a sense RUNX3 cDNA, in which the RUNX3 cDNA is over-expressed, and a cell strain having an antisense RUNX3 cDNA, in which the expression of the RUNX3 gene is inhibited are provided.

Also, the present invention provides a RUNX3 cDNA with tumor suppressor activity and its corresponding protein.

In the present invention, the RUNX3 gene is shown to play a crucial role in TGF-β-dependent apoptosis, using cell strains that either overexpress RUNX3 cDNA or selectively inhibit the expression of the RUNX3 gene.

Additionally, it is shown that the suppression of RUNX3 gene expression in various cell lines can be attributed to DNA methylation in the vicinity of exon 1 of the RUNX3 gene.

Further, the present invention provides a pharmaceutical composition including the RUNX3 gene or its protein.

Finally, the present invention provides uses of the RUNX3 gene and its proteins in the development of anticancer agents and diagnostic methods.

BRIEF DESCRIPTION OF THE DRAWINGS

FIG. 1a is a cDNA nucleotide sequence of the human RUNX3 gene with arrows denoting the primers used for RT-PCR analysis and bold letters denoting the translation initiation codon (ATG) and translation stop codon (TGA).

FIG. 1b continues the cDNA nucleotide sequence of the human RUNX3 gene from FIG. 1a.

FIG. 1c is an amino acid sequence deduced from the sequence of the cDNA of the human RUNX3 gene shown in FIG. 1a.

FIG. 2a is a nucleotide sequence showing CpG islands present in exon 1 of the human RUNX3 gene with a site used as a probe in genomic DNA Southern blot analysis denoted by underlining and a translation initiation codon (ATG) denoted by bold letters.

FIG. 2b continues the nucleotide sequence of the CpG islands present in exon 1 of the human RUNX3 gene from FIG. 2a.

FIG. 5c shows a comparison of cancerous masses excised from the mice sacrificed on the final day of the experiment.

DETAILED DESCRIPTION OF THE INVENTION

Figure 3:
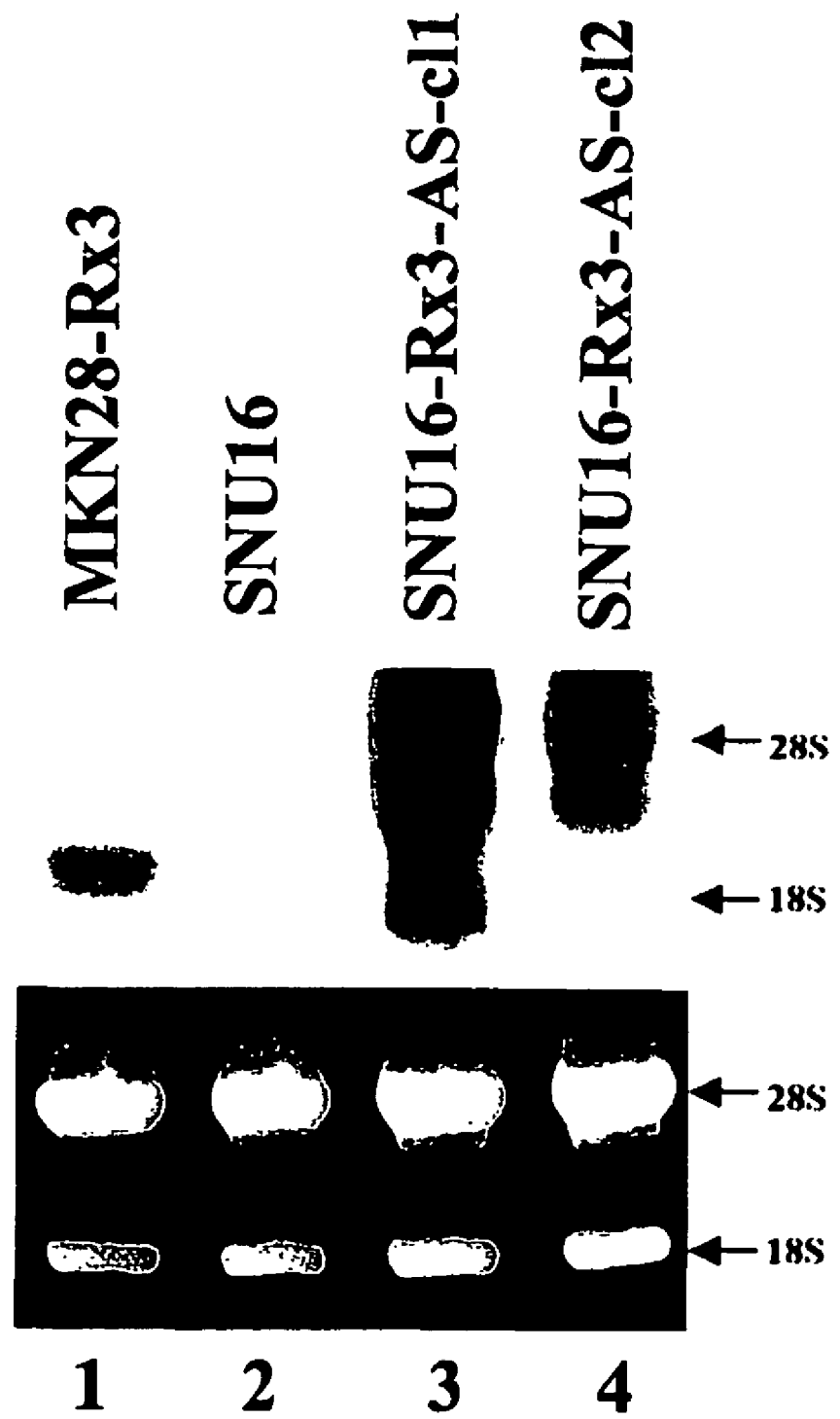
FIG. 3 is an autoradiogram resulting from Northern blotting analysis for determining whether SNU16-Rx3-AS-c11 and SNU16-Rx3-AS-c12, both having an antisense RUNX3 gene, and MKN28-Rx3, having a sense RUNX3 gene, express the antisense and sense RUNX3 genes.

In the present invention, the role of RUNX3 in cells is elucidated. For this purpose, a sense RUNX3 cDNA or an antisense RUNX3 cDNA is introduced into cells to establish strains over-expressing sense or antisense RUNX3 RNA, respectively.

Therefore, in one aspect of the present invention, cell lines are provided that harbor a sense RUNX3 cDNA or an antisense RUNX3 cDNA to excessively express the RUNX3 protein and to selectively inhibit the expression of the RUNX3 gene, respectively.

The human RUNX3 gene cloned by the present inventors in 1995 (Bae et al., Gene, 159 (2):245-248, 1995; cDNA nucleotide sequence GenBank Accession No. Z35278) was used to construct a plasmid vector capable of RUNX3 expression. The cDNA of the RUNX3 gene has the nucleotide sequence SEQ. ID. NO: 1. This cDNA has an open reading frame ranging from the translation start codon to the translation stop codon, and encodes a polypeptide consisting of 415 amino acids whose putative amino acid sequence is SEQ. ID. NO: 2 (see FIGS. 1a to 1c). A DNA fragment comprising CpG islands in the vicinity of exon 1 of the RUNX3 gene has the nucleotide sequence SEQ. ID. NO: 3 (see FIGS. 2a and 2b).

A 2,244 bp DNA fragment comprising a coding region of the RUNX3 gene cDNA SEQ. ID. NO: 1 (see FIG. 1a) was inserted in the sense direction into a pEF-BOS vector (Mizushima et al., Nucleic Acids Res., 18(17):5322, 1990) to construct a recombinant plasmid vector, named pEF-BOS-Rx3, which expresses a sense RUNX3 gene. Separately, the RUNX3 cDNA was inserted in the antisense orientation into a pEF-BOS vector to construct a recombinant vector, named pEF-BOS-Rx3-AS.

After the plasmid vector pEF-BOS-Rx3 was co-transfected with another vector bearing a neo resistance selection marker into various cancer cell strains, stable transfectants over-expressing the sense RUNX3 RNA were selected. In a preferred embodiment of the present invention, the pEF-BOS-Rx3 plasmid and a plasmid with a neo selection marker were co-transfected into the MKN28 strain (which does not express a RUNX3 gene) using Lipofectamine (Gibco-BRL), and the selection of transfectants was achieved by means of G418 resistance. The MKN28 strain that shows over-expression of the sense RUNX3 gene was named MKN28-Rx3 and deposited with the Korean Collection for Type Culture of Korea Research Institute of Bioscience and Biotechnology (KRIBB) under the deposition No. KCTC 0933BP on Jan. 9, 2001.

The strains that express the antisense RUNX3 RNA were established by co-transfecting the plasmid vector pEF-BOS-Rx3-AS and a plasmid with a selection marker into cells of the SNU16 gastric cancer cell line (Kim et al., J. Natl. Cancer Inst., 8(13):938-943, 1991) which has an inactivated p53 gene and a normal TGF-β gene system (Park et al., Proc. Natl. Acad. Sci. U.S.A., 91 (10):8772-8776, 1994). Stable transfectants were obtained in the same manner as above. Two transfectants which expressed the antisense RUNX3 RNA in excess were named SNU16-Rx3-AS-c11 and SNU16-Rx3-AS-c12, and deposited with the Korean Collection for Type Culture of KRIBB under the deposition Nos. KCTC 0934BP and KCTC 0935BP on Jan. 9, 2001.

To determine whether the transfectants MKN28-Rx3, SNU16-Rx3-AS-c11, and SNU16-Rx3-AS-c12 actually express the sense RUNX3 gene or the antisense RUNX3 gene, the RUNX3 cDNA of SEQ. ID. NO: 1 was used as a DNA probe for Northern blotting analysis. A RUNX3 transcript from the MKN28-Rx3 strain was detected as a single band at a position almost identical to that of 18S RNA, verifying the expression of RUNX3 mRNA in the cell. In contrast, antisense RUNX3 RNAs of various sizes were detected from SNU16-Rx3-AS-c11 and SNU16-Rx3-AS-c12 cells. In the control SUN16 strain, the expression of the endogenous RUNX3 gene was hardly detected by Northern blotting analysis (see FIG. 3).

In another aspect of the present invention, a RUNX3 gene and its product, which show tumor suppressor activity, are provided.

In the present invention, the function of the RUNX3 gene is elucidated by using the MKN28-Rx3 strain, which expresses the RUNX3 gene, and the SNU16-Rx-AS-11c and the SNU16-Rx-AS-12c strains, whose RUNX3 gene expression is selectively inhibited.

To analyze the role of RUNX3 in the TGF-β-induced programmed cell death (apoptosis), the SNU16-Rx3-AS-c11 and SNU16-Rx3-AS-c12 strains in which RUNX3 expression is selectively inactivated were treated with TGF-β1; normal SNU16 cells were used as a control. Counts of viable cells revealed that TGF-β1 induces apoptosis in the control strain, but not in the mutant strains. In detail, treatment with TGF-β1 killed all SNU16 cells within 2 days. However, treatment with TGF-β1 did not kill the SNU16-Rx3-AS-c11 and SNU16-Rx3-AS-c12 cells (see FIG. 4a). Accordingly, these results show that the RUNX3 gene is involved in the TGF-β1-induced cell death in SNU16 cells.

In the present invention, inventors also determine whether the mechanism of the RUNX3-dependent TGF-β1-induced cell death in SNU16 cells treated with TGF-β1 is via the apoptosis pathway or a necrosis pathway. Electrophoresis of DNA from cells killed through apoptosis yields specific apoptotic DNA bands. These bands are apparent in the DNA from SNU16 cells treated with TGF-β1 (see FIG. 4b Lanes 1 and 2). However, no apoptotic bands were observed in the DNA of the SNU16-Rx3-AS-c11 and SNU16-Rx3-AS-c12 cells (see FIG. 4b, Lanes 3 to 6). Therefore, TGF-β1 stimuli kill SNU16 cells through an apoptotic pathway, and RUNX3 is indispensable for this process.

It is known that TGF-β1-induced apoptosis is a very important mechanism for suppressing the progression of normal cells toward cancer, and that most of the factors involved in the TGF-β pathway have tumor suppressor activity (Chang et al., Cancer Res., 57(14):2856-2859, 1997). To examine the anticancer activity of RUNX3, a tumorigenesis assay was performed using nude mice. For the tumor suppressor activity assay, the cell lines are introduced into nude mice by subcutaneous injection, after which the cancerous masses formed are periodically measured for their external sizes. After the mice are sacrificed on the final day, the cancerous masses are excised for comparison.

The tumors formed in the nude mice grew at a higher rate in the mice injected with the cells expressing SNU16-Rx3-

Figure 5A:
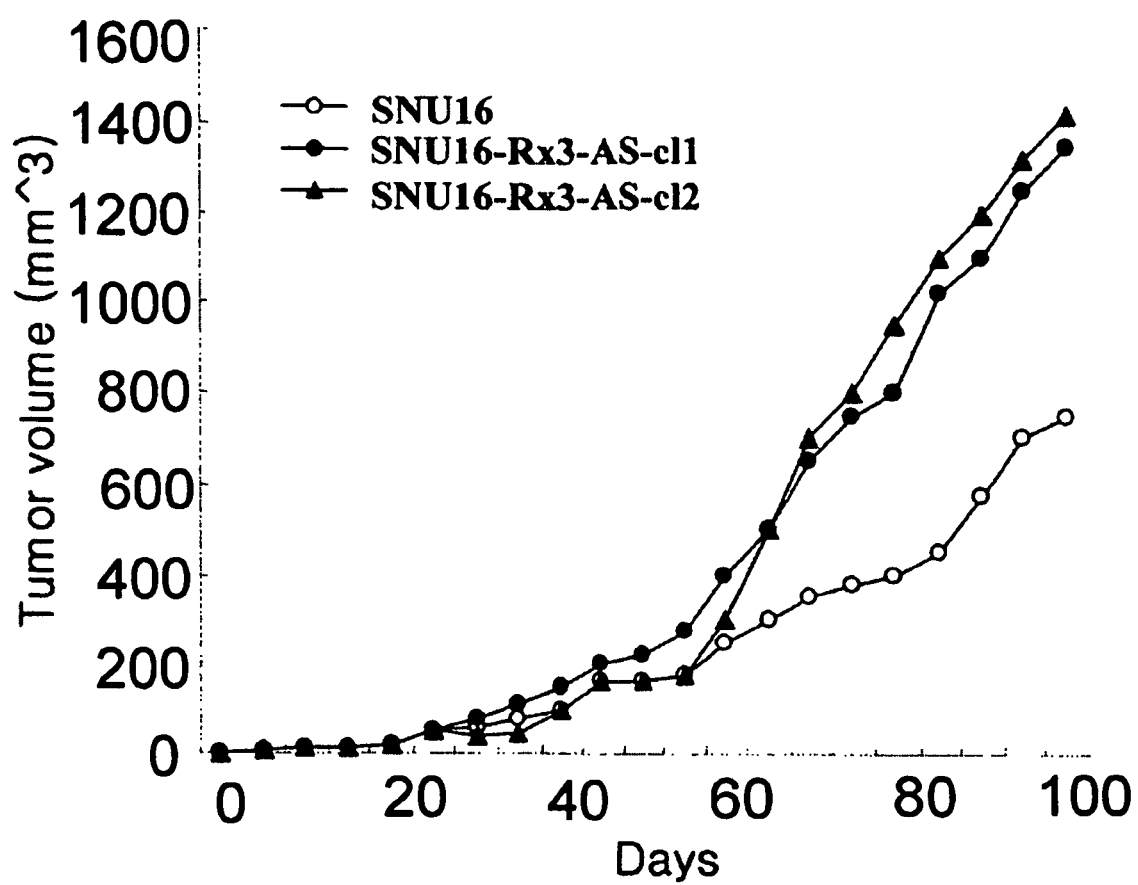
FIG. 5a is a graph showing that the size of the tumors formed in nude mice were measured periodically for over 98 days after the subcutaneous injection of SNU16-Rx3-AS-c11 and SNU16-Rx3-AS-c12, both having restricted RUNX3 expression due to the over-expression of the antisense RUNX3 gene therein; and control-SNU16 which expresses the RUNX3 gene normally.

AS-c11 or the SNU16-Rx3-AS-c12 than those in the mice injected with the control SNU16 cells (see FIG. 5a). In detail, the cancerous masses were measured on the final day. Those of the experimental group into which SNU16-Rx3-AS-c11 and SNU16-Rx3-AS-c12 had been injected were 1,600 mm$^3$ in volume, while those of the control group were about 800 mm$^3$. The cancerous masses were excised from the mice 98 days after the injection and compared to one another. The cancerous masses from the experimental group were remarkably larger than those from the control group (see FIG. 5c).

The tumorigenicity of control MKN28 cells and MKN28-Rx3 cells in which the sense RUNX3 RNA is expressed was also assayed, using nude mice in the manner described above for the SNU16 cells. Significantly reduced tumorigenesis was observed in the mice injected with MKN28-Rx3 cells compared to that of the mice injected with control MKN28 cells (see FIG. 5b). In detail, the cancerous masses of the control group were 600 mm$^3$ in volume on the final day, in contrast to those of the cancerous masses of the MKN28-Rx3-injected experimental group, which were found to be as small as 250 mm$^3$. This represents a reduction of tumor growth of 58%. The cancerous masses were excised from the mice 30 days after the injection and compared to one another (FIG. 5c).

These results demonstrate that the RUNX3 gene has tumor suppressor activity.

In the present invention, the RUNX3 gene was analyzed for its expression pattern in various cancer cell lines. Total RNAs were isolated from 15 gastric cancer cell lines and 17 lung gastric cancer cell lines and used to determine whether these cell lines produce RUNX3 mRNAs, by use of RT-PCR. The gastric cancer cell lines used in this RT-PCR were SNU1, SNU5, SNU719, NUGC3, MKN1, MKN7, MKN28, MKN45, MKN74, AGS, KatoIII, RF1, RF48, and AZ521. The lung cancer cell lines were NCI-H522, 86-2, A549, LK79, LK87, LCSC#1, LCSC#2, NCI-H23, NCI-H226, NCI-460, NCI-H322, Sq-19, NCI-H1915, NCI-H630, Hs 888Lu, Lu65, and LX-1. These cell lines were obtained from the Korean Research Institute of Bioscience and Biotechnology (KRIBB).

Figure 6A:
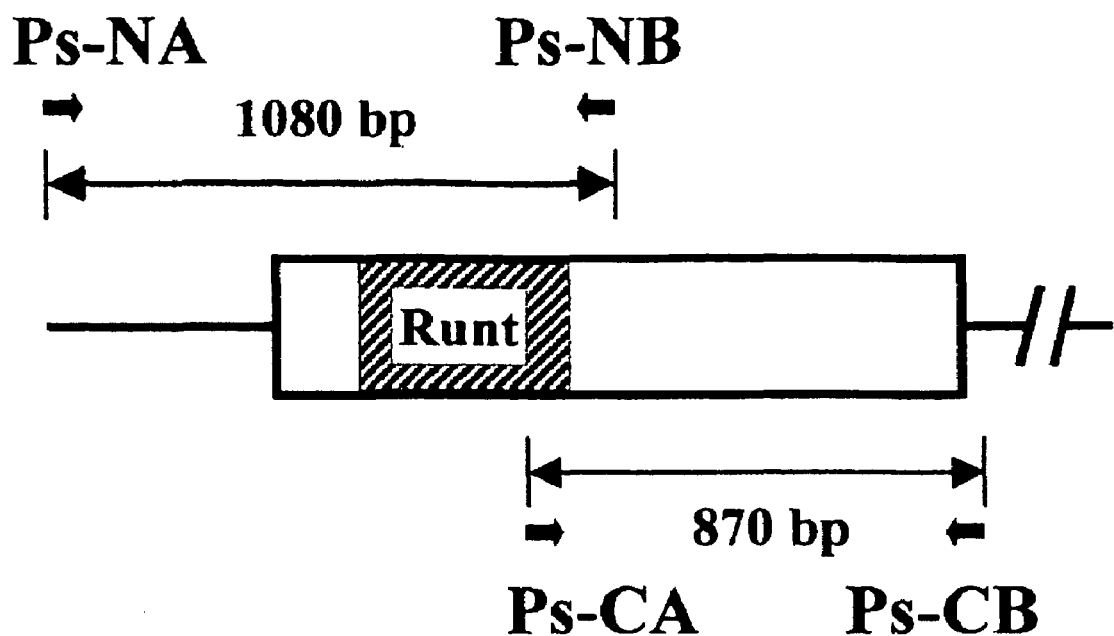
FIG. 6a is a schematic view showing the structure of the RUNX3 cDNA with arrows denoting the RT-PCR primer positions, and a striped box denoting the Runt domain, which plays an important role in binding of the RUNX3 protein to DNA.
Figure 6B:
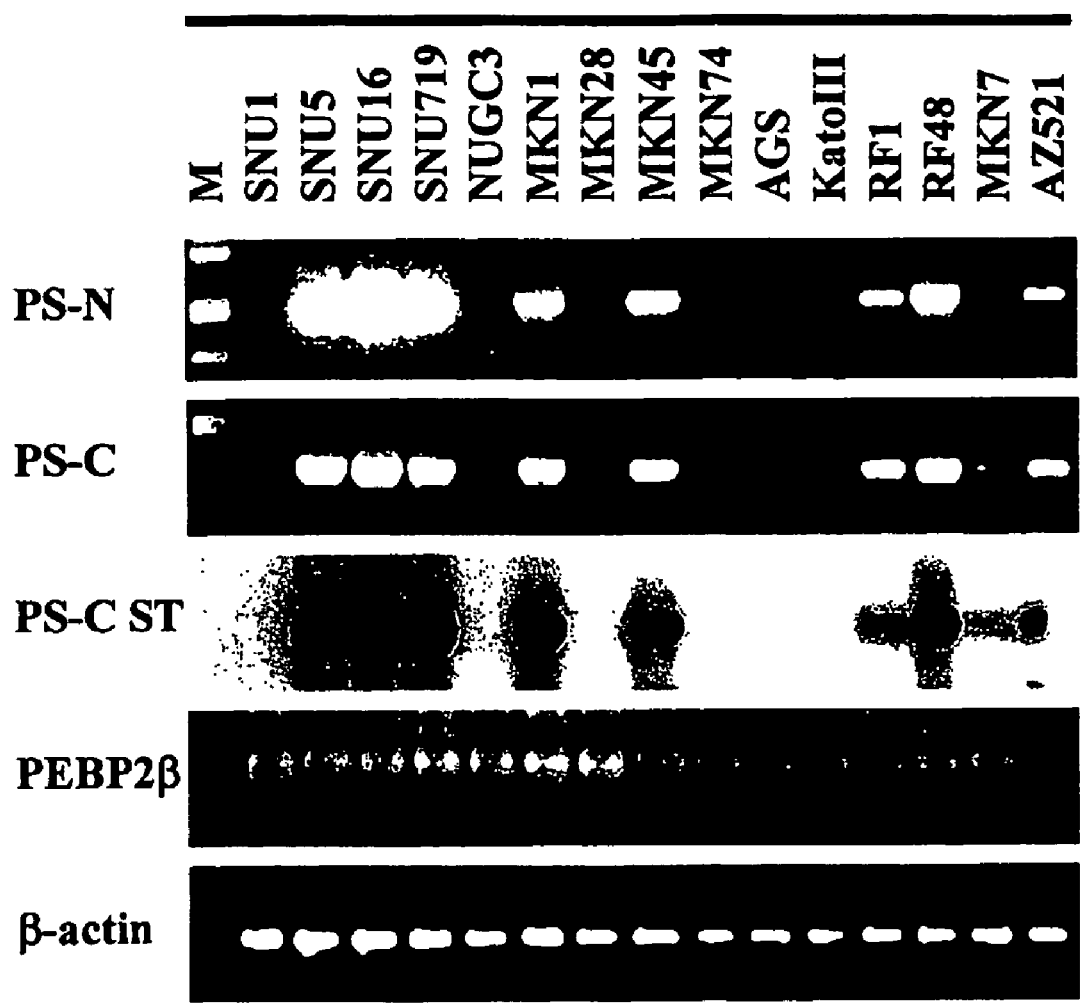
FIG. 6b shows the results of electrophoresis of RT-PCR products obtained from total RNAs of 15 gastric cancer cell lines by use of pairs of PS-N primers (PS-N), PS-C primers (PS-C), human PEBP2β/CBFB cDNA primers (PEBP2β), and human β-actin cDNA primers (β-actin), and the results of Southern blotting (PS-C ST). For the Southern blot analysis, RT-PCR products obtained by use of PS-C primers were hybridized with RUNX3 cDNA as a probe.

RT-PCR was conducted using two primer pairs, named PS-N and PS-C (FIG. 1a). Among the gastric cancer cell lines, SNU5, SNU16, SNU719, MKN1, MKN45, RF1, RF48, MKN7, and AZ521 were found to produce RT-PCR products with expected sizes (1,080 bp with the PS-N primer pair and 870 bp with the PS-C primer pair), although MKN7 produced RT-PCR products in very small quantities (FIG. 6b). In contrast, no RT-PCR products were obtained from the SNU1, NUGC3, MKN28, MKN74, AGS, and KatoIII cell lines when using either the PS-N primer pair or the PS-C primer pair.

Figure 6C:
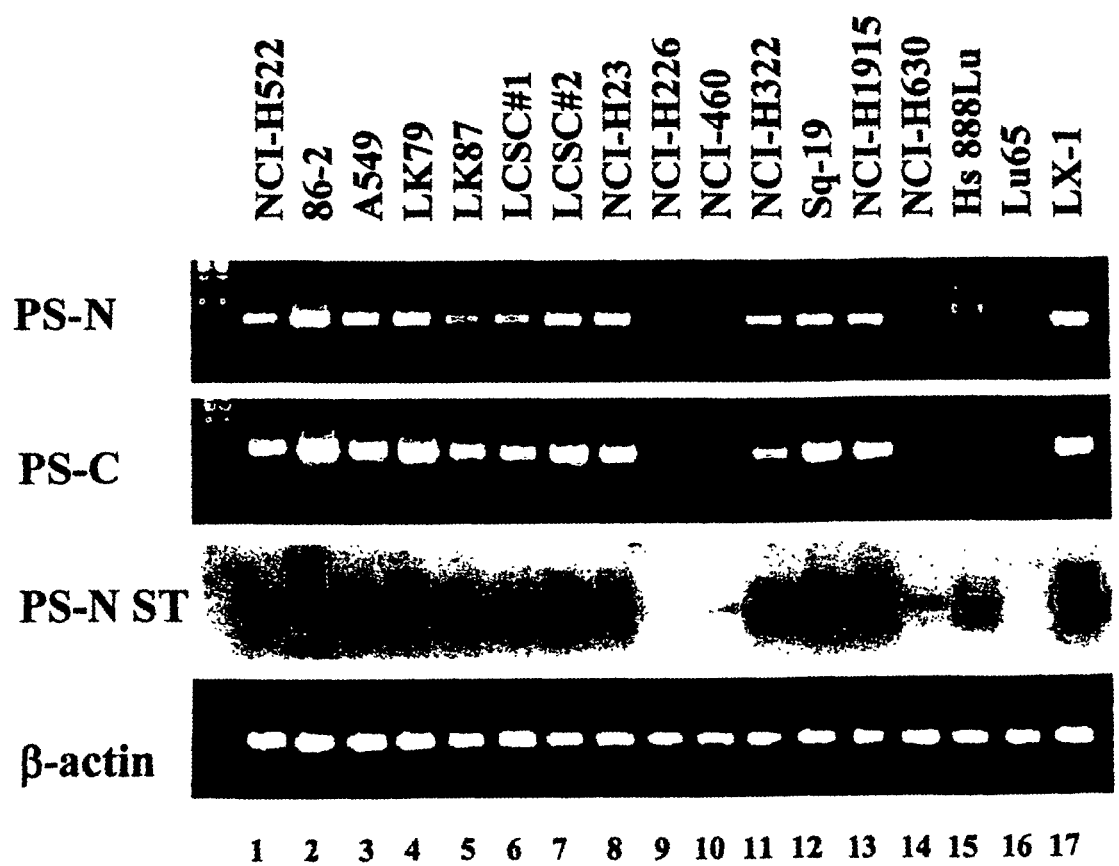
FIG. 6c shows the results of electrophoresis of RT-PCR products obtained from total RNAs of 17 lung cancer cell lines by use of pairs of PS-N primers (PS-N), PS-C primers (PS-C), and human β-actin cDNA primers (β-actin), to analyze the production of RUNX3 mRNA.

In the case of the lung cancer cell lines, the expression of the RUNX3 gene was found to be suppressed significantly in the HS888Lu cell line and completely in NCI-H226, NCI-460, NCI-H630, and Lu65 cell lines (see FIG. 6c).

Southern blotting analysis was used to verify that the RT-PCR products were amplified from the cDNA of the RUNX3 gene (see FIG. 6b, PS-3 ST). Additionally, the amplification of PEBP2β (see FIG. 6b PEBP2β) and β-actin cDNAs (see FIG. 6b, β-actin) from identical first cDNA strands was observed, indicating that the lack of amplification of RUNX3 cDNAs in the gastric cancer cell lines SNU1, NUGC3, MKN28, MKN74, AGS, KatoIII, NCI-H226, NCI-460, NCI-H630, and Lu65 can be attributed to a lack of expression of the RUNX3 gene in those cell lines.

Likewise, the low levels of the RT-PCR products in the MKN7 and Hs888Lu cell lines result from the low expression levels of the RUNX3 gene in the cell lines.

The above results show that the RUNX3 gene is remarkably or completely suppressed in about 47% of the gastric cancer cell lines and about 30% of the lung cancer cell lines. Therefore, the suppression of the RUNX3 gene expression can be an important diagnostic index in about 47% of gastric cancer cells and about 30% of lung cancer cells (in about 37% of the total number of gastric and lung cancer cell lines we examined).

Mutation analysis of the RUNX3 gene in cancer cell lines was performed using all exons of the RUNX3 gene, amplified from various cancer cell lines. No point mutation affecting the amino acid sequence was found. These results led to the conclusion that cancer cell lines in which the expression of the RUNX3 gene was not detected contain a normal RUNX3 gene, but do not express it. To determine whether the suppression of the RUNX3 gene expression can be attributed to DNA methylation, the correlation between the expression of the RUNX3 gene and the hypermethylation of CpG islands at loci near RUNX3 exon 1 was analyzed through genomic DNA Southern blotting using restriction enzymes sensitive to DNA methylation. Genomic DNAs isolated from cancer cell lines were separately treated with restriction enzymes which are unable to cut methylated DNA and enzymes that are able to cut DNA irrespective of methylation.

In one preferred embodiment of the present invention, SmaI, which cannot digest methylated DNA, and BamH1, which can digest DNA irrespective of its methylation, were used. The DNA was specifically protected from SinaI digestion in the gastric cancer cell lines whose RUNX3 gene expression was not detected, that is, the SNU1, NUGC3, MKN28, MKN74, AGS, and KatoIII cell lines. The MKN7 cell line in which the expression level was very low showed a partially methylated pattern (see FIG. 7a). These results suggest that the expression of the RUNX3 gene is closely correlated with DNA methylation at loci near RUNX3 exon 1 in cancer cell lines.

To examine further whether DNA methylation causes RUNX3 gene silencing, the influence of a DNA methyltransferase inhibitor and a histone deacetylase inhibitor on the reactivation of RUNX3 gene expression was analyzed. 5-aza-3-deoxycytidine (AZA, 300 nM) and trichostatin A (TSA, 1 mM) were used as DNA methylase and histone deacetylase inhibitors, respectively. Upon treatment with either the DNA methyltransferase inhibitor or the histone deacetylase inhibitor, the expression of the RUNX3 gene was induced (see FIG. 8). These results demonstrate that the hyper-methylation of CpG islands at loci near exon 1 of the RUNX3 gene is responsible for the suppression of RUNX3 gene expression in about 37% of the cancer cells. This result also indicates that agents capable of promoting the reactivation of the RUNX3 gene can be developed from DNA methyltransferase inhibitors or histone deacetylase inhibitors and used as anticancer agents.

According to the present invention, therefore, the product of the RUNX3 gene is involved in TGF-β1-dependent apoptosis and shows tumor suppressor activity. The expression of the RUNX3 gene is suppressed in a substantial portion of the cancer cells by the hyper-methylation of CpG islands at loci near exon 1 of the gene.

In a further aspect of the present invention, expression vectors are provided that are capable of expressing RUNX3 cDNA, and pharmaceutical compositions are provided that comprise proteins of the genes as pharmaceutically effective ingredients.

The pharmaceutical compositions of the present invention can be used for the diagnosis, prophylaxis, and treatment of the diseases attributed to abnormal TGF-β-dependent apoptosis, including gastric and lung cancers.

As the pharmaceutically effective ingredients, RUNX3 cDNA, RUNX3 RNA, or proteins produced therefrom may be used. Expression vectors capable of expressing the RUNX3 gene are preferable because they can produce RUNX3 proteins continuously if they are injected. Where a pharmaceutical composition comprising such an expression vector is injected into a bio-tissue via a parenteral route, the bio-tissue can produce RUNX3. That is, the RUNX3 gene of the present invention or an expression vector anchoring the RUNX3 gene can be used as a pharmaceutically effective ingredient of a pharmaceutical composition for use in gene therapy.

Administration of the RUNX3 cDNA of the present invention and/or the RUNX3 RNA or the RUNX3 protein produced therefrom may take an oral or a parenteral route, with preference for parenteral injection.

The expression vector comprising the RUNX3 gene or the RUNX3 protein produced therefrom may be administered in various oral or parenteral dosage forms. For the formulation of the pharmaceutically useful ingredient, diluents, expedients, and/or carriers, such as fillers, thickeners, binders, wetting agents, disintegrating agents, surfactants, etc., may be used. Solid formulations for oral administration may be formed into pills, tablets, powders, granules, capsules, etc. These solid formulations may comprise at least one expedient, such as starch, calcium carbonate, sucrose, lactose, gelatin, etc. In addition to simple expedients, lubricants such as magnesium stearate and talc may be used. Liquid formulations for oral administration may be exemplified by suspensions, internal solutions, emulsions, syrups, etc. These liquid formulations may comprise various expedients, for example, wetting agents, sweeteners, odorants, and preservatives, as well as simple diluents such as water, liquid paraffin, etc. Examples of formulations for parenteral administration include sterile aqueous solutions, non-aqueous solutions, suspensions, emulsions, freeze-dried agents, and suppositories. For the formation of non-aqueous solutions or suspensions, vegetable oils such as polypropylene glycol, polyethylene glycol, and olive oil, and an injectable ester such as ethyloleate may be used. As bases of suppositories, witepsol, microgol, Tween 61, cacao oil, lauringe, and glycerogelatin may be used. In order to help the absorption of the pharmaceutically useful ingredient into cells, liposomal dosage forms may be used.

The therapeutically effective dose of the pharmaceutically effective ingredients is within the range of 0.002 to 1 mg/kg of body weight and preferably within the range of 0.02 to 0.2 mg/kg of body weight for RUNX3 cDNA, within the range of 0.001 to 0.5 mg/kg of body weight and preferably within the range of 0.01 to 0.1 mg/kg of body weight for RUNX3 RNA, and within the range of 0.04 to 4 mg/kg and preferably within the range of 0.4 to 1 mg/kg of body weight for RUNX3 protein.

In accordance with a further aspect of the present invention, uses of the RUNX3 gene and its proteins in the development of anticancer agents and the diagnosis of cancers are provided.

As described above, the RUNX3 gene of the present invention shows excellent tumor suppressor activity and is indispensable for TGF-β-dependent apoptosis. The expression of RUNX3 is suppressed in about 47% of gastric cancer cell lines and about 30% of lung cancer cell lines (in about 37% of the total number of gastric and lung cancer cell lines). In addition, the suppression of RUNX3 gene expression is attributed to abnormal DNA methylation of CpG islands located at loci near exon 1 of the RUNX3 gene. Further, treatment with a DNA methylase inhibitor or a histone deacetylase inhibitor can induce the expression of the RUNX3 gene. Therefore, the RUNX3 gene of the present invention and proteins produced therefrom can be utilized in developing not only anticancer agents, but also diagnostic methods for detecting cancers, in which abnormal DNA methylation of CpG islands at the loci near exon 1 of the RUNX3 gene is measured.

Based on the facts presented in the present invention, pharmaceutical compositions comprising materials capable of regulating the methylation of a nucleotide sequence that includes CpG islands near RUNX3 exon 1 can be provided for the prophylaxis and treatment of cancers as pharmaceutically effective ingredients.

A method for diagnosing cancers characterized by detecting the methylation of the nucleotide sequence containing CpG islands present near exon 1 of the RUNX3 gene comprises the steps of:

isolating genomic DNA from a tumor tissue of a subject;

digesting the genomic DNA with a restriction enzyme sensitive to DNA methylation;

separating the genomic DNA digests on an agarose gel by electrophoresis and transferring them onto a membrane;

hybridizing the genomic DNA digests with a radiolabeled DNA probe for the RUNX3 gene; and exposing the membrane to a film to detect the expression of the RUNX3 gene.

In accordance with another embodiment of the present invention, a method for diagnosing cancers comprises the steps of:

Isolating genomic DNA from blood or a tumor tissue of a subject;

digesting the genomic DNA with a restriction enzyme sensitive to DNA methylation;

performing a polymerase chain reaction (PCR) with the genomic DNA digests serving as templates and with parts of the nucleotide sequence of SEQ. ID. NO: 3 serving as primers;

separating the PCR products on an agarose gel by electrophoresis to detect the amplification of a DNA sequence of interest.

The diagnostic method using PCR is based on the principle that PCR products are obtained if the DNA region of interest is methylated; otherwise, the products are not obtained.

In accordance with a still further aspect of the present invention, a biological microchip for use in cancer diagnosis is provided, which comprises a part of the RUNX3 cDNA SEQ. ID. NO: 1 or proteins produced therefrom.

Generally, a biological microchip for the diagnosis of diseases, which is based on principles of molecular biology and electronic engineering, has tens to tens of thousands of DNAs or proteins integrated on a small chip. Thanks to the high level of integration, the biological microchip can be used to search for at least hundreds of genes or proteins within a short period of time. Therefore, the biological chip can be used to perform a search for novel genes or to diagnose diseases very rapidly and simply, compared to conventional bioengineering techniques. Biological chips can be classified into oligonucleotide chips and cDNA chips according to the genetic materials integrated thereon, and they can be fabricated according to use, for example, genes to be searched, diseases to be diagnosed, etc. Microchips using parts of the RUNX3 cDNA nucleotide sequence or antibodies against proteins produced from the RUNX3 cDNA fragments can be used for the diagnosis of various cancers, including gastric and lung cancers.

EXAMPLES

A better understanding of the present invention may be obtained in light of the following examples which are set forth to illustrate, but are not to be construed to limit, the present invention.

Example 1

Establishment of the SNU16-Rx3-AS and MKN28-Rx3 Cell Strains

To elucidate the function of the RUNX3 gene in vivo, cell strains capable of over-expressing a sense RUNX3 gene and an antisense RUNX3 gene were established as follows.

1-1 Construction of Expression Plasmid Vectors Containing Sense and Antisense RUNX3 Genes The human RUNX3 gene cloned by the present inventors in 1995 (Bae et al., Gene, 159 (2):245-248, 1995; cDNA nucleotide sequence GenBank Accession No. Z35278) was used to construct plasmid vectors capable of expressing RUNX3. The cDNA of the RUNX3 gene has the nucleotide sequence SEQ. ID. NO: 1 with an open reading frame ranging from the translation start codon to the translation stop codon, which encodes a polypeptide consisting of 415 amino acids whose putative amino acid sequence is SEQ. ID. NO: 2 (FIGS. 1a to 1c). A DNA fragment comprising CpG islands present in the vicinity of exon 1 of the RUNX3 gene has the nucleotide sequence SEQ. ID. NO: 3 (FIGS. 2a and 2b).

A 2,244 bp BamHI DNA fragment (FIG. 1a) comprising a coding region out of the cDNA of the RUNX3 gene SEQ. ID. NO: 1 was inserted in the sense direction into a PEF-BOS vector (Mizushima et al., Nucleic Acids Res., 18(17): 5322, 1990) at an XbaI site to construct a recombinant plasmid vector, named pEF-BOS-Rx3, which expresses a sense RUNX3 gene.

Separately, the RUNX3 cDNA was inserted in the antisense direction into a pEF-BOS vector at an XbaI site to construct a recombinant vector, named pEF-BOS-Rx3-AS.

1-2 Stable Transfection

The plasmid vector pEF-BOS-Rx3, established in Example 1-1, and pcDNA3.1, which contains a neo selection marker, were co-transfected into the MKN28 strain by the Lipofectamine (Gibco BRL) method as specified by the manufacturer. MKN28 does not endogenously express RUNX3. Stable transfectants that harbored pEF-BOS-Rx3 (sense RUNX3 RNA) were selected in the presence of G418. The MKN28 strain overexpressing sense RUNX3 RNA was named MKN28-Rx3 and deposited with the Korean Collection for Type Culture of Korea Research Institute of Bioscience and Biotechnology (KRIBB) under the deposition No. KCTC 0933BP on Jan. 9, 2001.

The strains capable of expressing the antisense RUNX3 gene were established by co-transfecting the plasmid vector pEF-BOS-Rx3-AS along with pcDNA3.1, which contains a selection marker, into the SNU16 strain, a gastric cancer cell line (Kim et al., J. Natl. Cancer Inst., 8(13):938-943, 1991) that has an inactivated p53 gene and a normal TGF-β signaling system (Park et al., Proc. Natl. Acad. Sci. U.S.A., 91 (10):8772-8776, 1994). Stable transfectants were obtained in the same manner as above. Two transfectants that excessively express the antisense RUNX3 gene to selectively inhibit the expression of the RUNX3 gene were named SNU16-Rx3-AS-c11 and SNU16-Rx3-AS-c12, and deposited with the Korean Collection for Type Culture of KRIBB under the deposition Nos. KCTC 0934BP and KCTC 0935BP on Jan. 9, 2001.

For comparison, pcDNA3.1 was transfected alone into SUN16 and MKN28, which were cultured in the presence of G418. The clones obtained were used as controls, named control-SNU16 and control-MKN28.

1-3 Northern Blot Analysis

To determine whether the transfectants MKN28-Rx3, SNU16-Rx3-AS-c11, and SNU16-Rx3-AS-c12, established in Example 1-2, express the sense RUNX3 gene or the antisense RUNX3 gene in large quantities, Northern blotting analysis was conducted.

Total cellular RNA was prepared from each cell strain according to a standard method (Sambrook et al., Molecular Cloning, a laboratory manual, $2^{nd}$ Ed., 1988, Cold Spring Harbor Laboratory). Five micrograms of each RNA preparation was separated on a 1.2% formaldehyde/agarose gel by electrophoresis and transferred onto a Hybond-$N^+$ nylon membrane (Amersham). The RUNX3 cDNA of SEQ. ID. NO: 1 (Bae et al., Gene, 159 (2):245-248, 1995) was labeled with [$\alpha$-$^{32}$P]dCTP for use as a probe for blotting analysis. Hybridization was conducted by incubating the Hybond-$N^+$ nylon membrane and the radiolabeled RUNX3 DNA probe at 65° C. for 16 hours in 5× Denhardt's solution comprising 5×SSPE, 0.5% SDS and 100 mg/ml of salmon sperm. Afterwards, the nylon membrane was washed twice with 2×SSPE/0.1% SDS solution at room temperature for 15 min and twice with 0.1×SSPE/0.1% SDS solution at 65° C. for 15 min. The membrane was exposed to Kodak XAR-5 film for 16 hours at −70° C. to yield an autoradiogram.

On the autoradiogram obtained from the MKN28-Rx3 strain, a single band was observed at a position close to that of 18S RNA, verifying the expression of the RUNX3 cDNA in the strain. In contrast, SNU16-Rx3-AS-c11 and SNU16-Rx3-AS-c12 cells, which harbor the antisense RUNX3 cDNA, were found to give antisense RUNX3 gene transcripts of various sizes as detected by multiple bands on the autoradiogram. In the control-SUN16 strain, the expression of the endogenous RUNX3 gene was not detected by Northern blotting analysis (see FIG. 3).

Example 2

Cell Death Effect of TGF-β and Role of the RUNX3 Gene in TGF-β-Induced Cell Death 2-1 Cell Death Effect of TGF-β

SNU16 cells, which normally express the RUNX3 gene, and SNU16-Rx3-AS-c11 and SNU16-Rx3-AS-c12 cells in which an antisense RUNX3 cDNA is over-expressed to selectively inhibit the expression of the normal RUNX3 gene, were individually treated with TGF-β1 (1 ng/ml), after which viable cells were counted over a period of time. The results are shown in FIG. 4a.

Figure 4A:
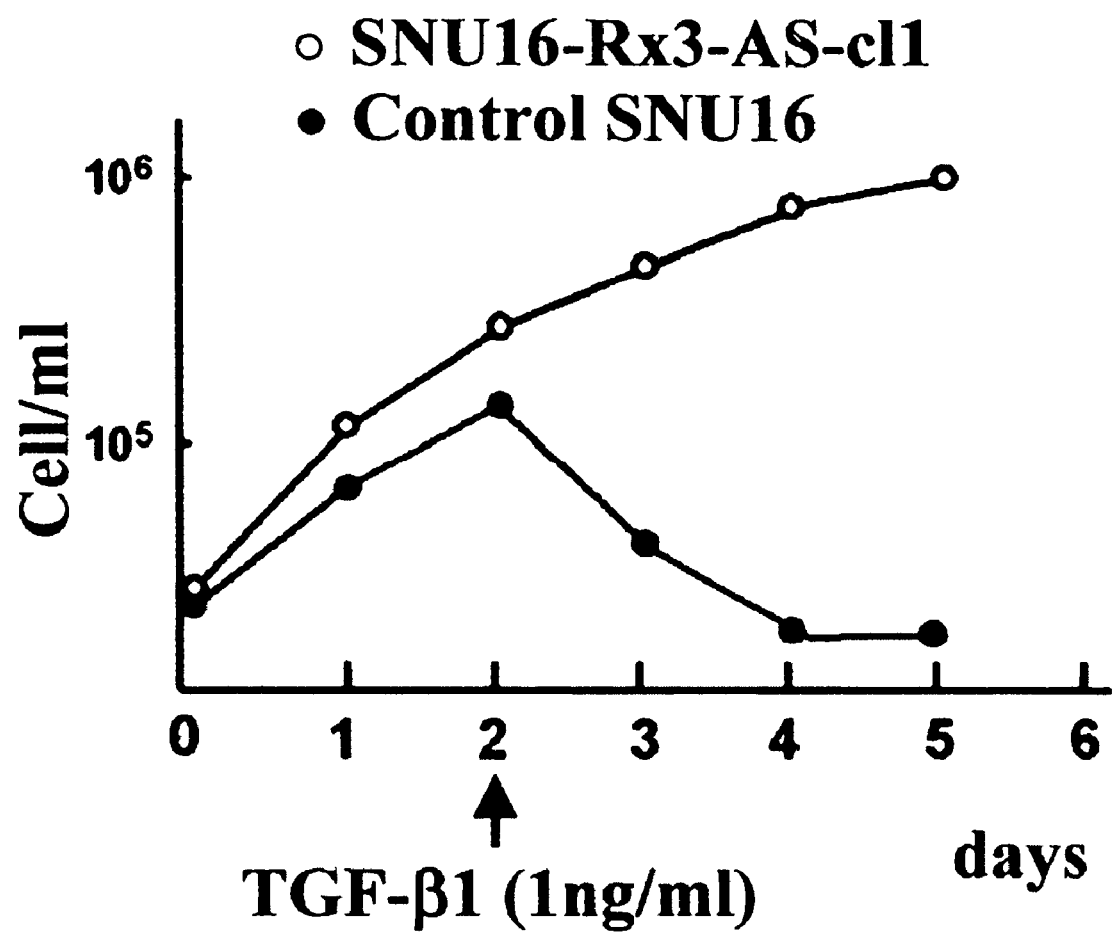
FIG. 4a is a graph in which counts of viable SNU16-Rx3-AS-c11 cells are plotted with regard to time, along with those of the control SNU16 cells, after treatment with 1 ng/ml of TGF-β to analyze TGF-β-induced cell death.

As seen in FIG. 4a, the TGF-β1 treatment induced cell death in SNU16 cells. Almost all SNU16 cells were killed within 2 days after treatment with TGF-β1 at a concentration of 1 ng/ml. However, the SNU16-Rx3-AS-c11 cells, in which the antisense RUNX3 gene was excessively expressed to selectively inhibit the expression of the RUNX3 gene, were not killed after treatment with TGF-β1. These results suggest that the RUNX3 gene is involved in TGF-β1-induced cell death in SNU16 cells.

2-2 Role of RUNX3 Gene in TGF-β Induced Cell Death.

Cells dying through the programmed cell death pathway reveal a distinct pattern of DNA bands when electrophoresed in an agarose gel. After being treated with 1 ng/ml TGF-β1 for 6 hours, the control-SNU16, SNU16-Rx3-AS-c11, and SNU16-Rx3-AS-c12 strains were lysed to isolate genomic DNAs according to a standard method (Sambrook et al., 1988, Molecular Cloning: a laboratory manual, $2^{nd}$ Ed. Cold Spring Harbor Laboratory, Cold Spring Harbor, N.Y., USA). 0.2 µg of each of the genomic DNA preparations was electrophoresed on a 1.5% agarose gel and visualized with ethidium bromide under UV light. The results are given in FIG. 4b.

Figure 4B:
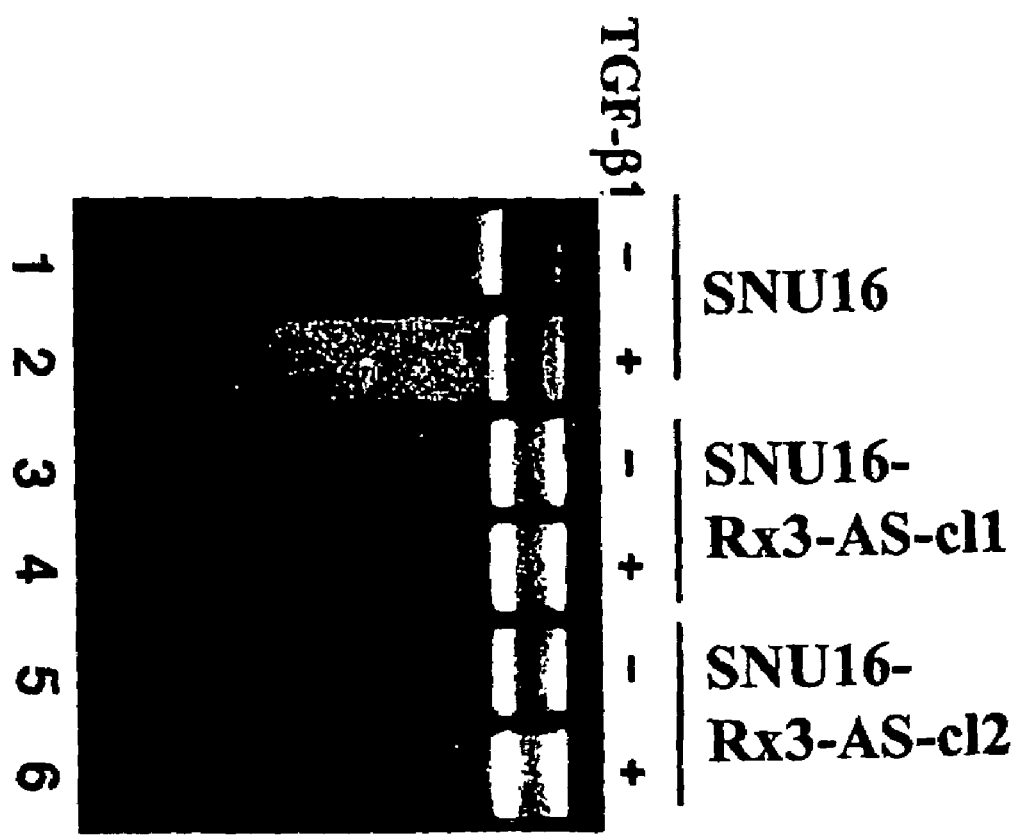
FIG. 4b is a photograph showing the results of the electrophoresis of the genomic DNAs obtained from SNU16, SNU16-Rx3-AS-c11, and SNU16-Rx3-AS-c12 after treatment with 1 ng/ml of TGF-β1 for 6 hours so as to determine whether RUNX3 is involved in the TGF-β-induced programmed cell death pathway.

As seen in this figure, apparent programmed cell death-specific apoptotic DNA bands were formed from the SNU16 cells treated with TGF-β1 (FIG. 4b, lanes 1 and 2). No apoptotic bands were observed in the DNA from SNU16-Rx3-AS-c11 and SNU16-Rx3-AS-c12 cells, both of which over-express the antisense RNX3 gene, and therefore have a selective reduction in RUNX3 expression (FIG. 4b, lanes 3 to 6).

We concluded from these results that SNU16 cells are killed by TGF-β1 stimuli through an apoptotic pathway and that RUNX3 is required for the process.

Example 3

Sugpressive Activity of RUNX3 Against Tumorigenicity

It is known that TGF-β1-induced apoptosis is a very important mechanism for suppressing the progression of normal cells toward cancer and that most of the factors in the TGF-β1 pathway have tumor suppressor activity. The RUNX3 gene was assayed for tumor suppressor activity using nude mice, with the expectation that an anticancer effect would be seen.

To this end, the SNU16-Rx3-AS-c11 and SNU16-Rx3-AS-c12 strains, in which RUNX3 gene expression is selectively inhibited and the control-SUN16 strain were suspended in 0.85% phosphate buffered saline (PBS) at a density of $3\times10^7$ cells/ml, and 0.3 ml of each suspension was subcutaneously injected into groups of nude mice. Separately, the MKN28-Rx3 strain that shows over-expression of the sense RUNX3 RNA and the control-MKN28 strain were suspended in 0.85% PBS at a density of $5\times10^7$ cells/ml, and 0.3 ml of each suspension was subcutaneously injected into other groups of nude mice. Each strain clone was administered to 9 nude mice, which constituted one group. The tumorigenicity of MKN28-Rx3 and control MKN-28 strains was observed for 37 days after the injection. The tumorigenicity of SNU16-Rx3-AS-c11, SNU16-Rx3-AS-c12, and control-SNU16 cells was monitored for 98 days. During these time periods, the cancerous masses that formed were periodically measured for their external sizes. On the final days, the mice were sacrificed to excise the cancerous masses for comparison.

It was observed that tumors developed at higher rates in the mice into which the SNU16-Rx3-AS-c11 or the SNU16-Rx3-AS-c12 cells were injected than the mice into which the control SNU16 cells were injected, as shown in FIG. 5a. In detail, cancerous masses formed in the control SNU16 cell-injected group were measured to be 800 mm³ in volume at the final day. In contrast, cancerous masses of the groups into which SNU16-Rx3-AS-c11 and SNU16-Rx3-AS-c12 were injected were measured at 1,600 mm³ in volume, twice as large as those of the control group. Ninety-eight days after the injection, the cancerous masses were excised from the mice and compared to one another. The cancerous masses from the experimental group were remarkably larger than those from the control group, as seen in FIG. 5c.

Figure 5B:
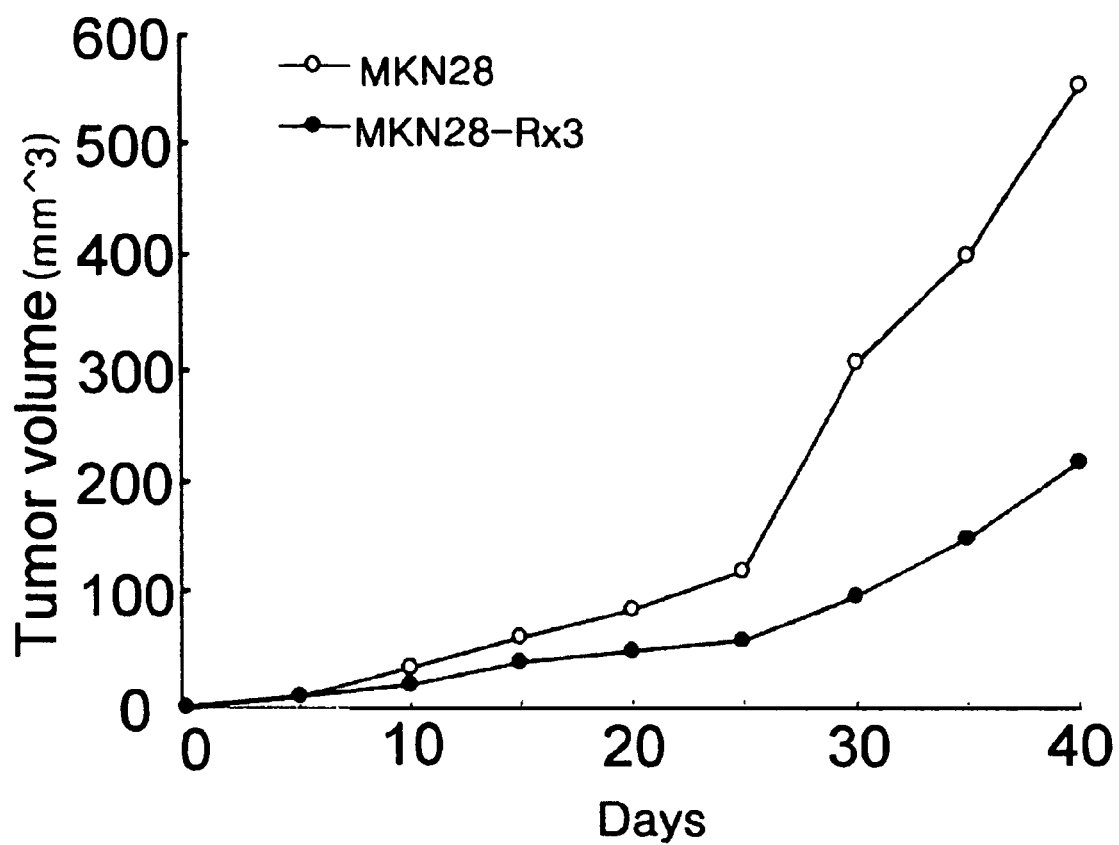
FIG. 5b is a graph in which tumors formed in nude mice were measured for size periodically for over 37 days after the subcutaneous injection of control MKN28, which does not express the RUNX3 gene, and MKN28-Rx3, in which a RUNX3 cDNA is expressed.

MKN28-Rx3 cells, in which the sense RUNX3 gene is expressed, and control MKN28 cells were also assayed for tumor suppressor activity using nude mice in the same manner as was used for the SNU16 cells. Mice injected with MKN28-Rx3 cells exhibited significantly reduced tumorigenesis compared to the mice injected with the control MKN28 cells, as shown in FIG. 5b. In detail, the cancerous masses of the control group were measured at 600 mm³ in volume on the final day. In contrast, the cancerous masses of the MKN28-Rx3-injected experimental group were found to be as small as 250 mm³, demonstrating that the tumor growth was reduced by 58%. Thirty days after the injection, the cancerous masses were excised from the mice and compared to one another. The cancerous masses excised from the MKN28-Rx3-injected experimental group were macroscopically smaller than those excised from the control group (FIG. 5c).

Taken together, these results demonstrate that the RUNX3 gene has tumor suppressor activity.

Example 4

Analysis of the Expression Pattern of the RUNX3 Gene in Cancer Cells 4-1 RT-PCR Analysis The expression pattern of the RUNX3 gene was analyzed in various cancer cell lines by RT-PCR. Total RNAs were isolated from 15 gastric cancer cell lines and 17 lung cancer cell lines and used to determine whether these cell lines produce RUNX3 mRNAs. The gastric cancer cells used in this analysis were SNU1, SNU5, SNU719, NUGC3, MKN1, MKN7, MKN28, MKN45, MKN74, AGS, KatoIII, RF1, RF48, and AZ521. The lung cancer cell lines were NCI-H522, 86-2, A549, LK79, LK87, LCSC#1, LCSC#2, NCI-H23, NCI-H226, NCI-460, NCI-H322, Sq-19, NCI-H1915, NCI-H630, Hs 888Lu, Lu65, and LX-1. All were obtained from the Korean Collection for Type Culture of Korea Research Institute of Bioscience and Biotechnology (KRIBB).

Total RNA was isolated from each cancer cell line, according to a standardized single-step guanidium method (Sambrook et al., Molecular Cloning: a laboratory manual, $2^{nd}$ Ed., 1988, Cold Spring Harbor Laboratory). Using a Superscript kit (Gibco BRL) according to the manufacturer's protocol, reverse transcription was performed to prepare cDNA from the isolated total RNA with oligo-dTs serving as primers. Based on the cDNA, the RUNX3 gene was amplified by RT-PCR to determine the production of RUNX3 mRNA. For this RT-PCR, two pairs of PCR primers, PS-N and PS-C, were synthesized, which were composed of a set of the sense primer PS-NA SEQ. ID. NO: 4 and the antisense primer PS-NB SEQ. ID. NO: 5 and a set of the sense primer PS-CA SEQ. ID. NO: 6 and the antisense primer PS-CB SEQ. ID. NO: 7. The nucleotide sequences of these two pairs of PCR primers were designed on the basis of the cDNA nucleotide sequence of the RUNX3 gene SEQ. ID. NO: 1 (FIG. 5a).

For comparison, PEBP2β/CBFB cDNA and β-actin cDNA were used as controls in the RT-PCR. To amplify the controls, a primer pair for PEBP2β/CBFB, consisting of the sense primer h-β5 SEQ. ID. NO: 8 and the antisense primer h-β3 SEQ. ID. NO:9, and a primer pair for β-actin, consisting of the sense primer h-actin 5 SEQ. ID. NO: 10 and the antisense primer h-actin 3 SEQ. ID. NO: 11, were synthesized. Nucleotide sequences of these primer pairs were designed on the basis of human PEBP2β cDNA and β-actin cDNA nucleotide sequences.

In a thermal cycler, such as "Model 9600" manufactured by Perkin-Elmer Cetus, RT-PCR was started with a 95° C. pre-denaturation of 50 μl of each PCR solution for 2 min and carried out with 30 cycles of denaturing at 95° C. for 15 sec, annealing at 50° C. for 1 min, and extending at 72° C. for 1 min. After completion of the RT-PCR, 5 μl of the RT-PCR product was electrophoresed on a 1.2% agarose gel and dyed with ethidium bromide for observation under UV light.

Among the gastric cancer cell lines, SNU5, SNU16, SNU719, MKN1, MKN45, RF1, RF48, MKN7, and AZ521 were found to produce RT-PCR products with the expected sizes (1,080 bp with the PS-N primer pair and 870 bp with the PS-C primer pair). However, MKN7 produced RT-PCR products in very small quantities, as shown in FIG. 6b. No RT-PCR products were obtained from the SNU1, NUGC3, MKN28, MKN74, AGS, and KatoIII cell lines when using either the PS-N primer pair or the PS-C primer pair.

Among the 17 lung cancer cell lines, expression of the RUNX3 gene was suppressed significantly in the HS888Lu cell line and completely in the NCI-H226, NCI-460, NCI-H630, and Lu65 cell lines, as shown in FIG. 6c.

4-2 DNA Southern Blot Analysis

Southern blotting analysis was conducted to verify the amplification of the RT-PCR products from the cDNA of the RUNX3 gene. The RT-PCR products were run on a 1.5% agarose gel under an electric field and the separated DNA fragments were transferred onto a Hybond-N+ nylon membrane.

Using the 2,244 bp BamHI fragment of the RUNX3 cDNA as a probe, hybridization was conducted in the same manner as in the Northern blotting analysis of Example 1-3, followed by autoradiography on XAR-5 films. The results are given in FIG. 6b.

As apparent from the autoradiogram, the RT-PCR products were amplified from the RUNX3 cDNA (PS-3 ST). In addition, the amplification of PEBP2β and β-actin cDNAs from identical first cDNA strands was observed, indicating that the lack of amplification of RUNX3 cDNAs in the gastric cancer cell lines SNU1, NUGC3, MKN28, MKN74, AGS, KatoIII, NCI-H226, and lung cancer cell lines, NCI-460, NCI-H630, and Lu65 can be attributed to a lack of expression of the RUNX3 gene in those cell lines. Likewise, the low levels of the RT-PCR products in the MKN7 and Hs888Lu cell lines result from the low expression levels of the RUNX3 gene in those cell lines.

From the above results, it is apparent that the RUNX3 gene is remarkably or completely suppressed in about 47% of the gastric cancer cell lines and about 30% of the lung cancer cell lines. Because TGF-β-induced apoptosis does not occur and the tumorigenicity of cancer cells is increased in the substantial absence of RUNX3, the suppression of RUNX3 gene expression can be an important diagnostic index in about 47% of gastric cancer cells and about 30% of lung cancer cells (in about 37% of the total cancer cells examined).

Example 5

Analysis of DNA Methylation Around Exon 1 of the RUNX3 Gene in Cancer Call Lines 5-1 Analysis of DNA Methylation by Southern Blotting Analysis of Genomic DNA To determine whether the suppression of RUNX3 gene expression was caused by DNA methylation, correlation between the expression of the RUNX3 gene and the hyper-methylation of CpG islands at loci near RUNX3 exon 1 was analyzed through genomic DNA Southern blotting using restriction enzymes sensitive to DNA methylation.

Genomic DNAs were isolated from cancer cell lines according to a standardized SDS/protease K method (Sambrook et al., 1989). The isolated genomic DNAs were treated with a restriction enzyme that is unable to cut methylated DNA (SmaI), and separately, with one that is able to cut DNA irrespective of methylation (BamHI). The restriction enzyme digests were electrophoresed on a 1.5% agarose gel and then transferred onto a Hybond-N+ membrane. A genomic DNA NheI/MluI fragment comprising CpG islands of the RUNX3 gene was used as a DNA probe (FIG. 7b), and hybridization was carried out in the same manner as in the Northern blotting analysis of Example 1-3, followed by autoradiography on XAR-5 films. The genoinic DNA was isolated from human genome DNA libraries with the RUNX3 cDNA of SEQ. ID. NO: 1 serving as a probe.

Figure 7A:
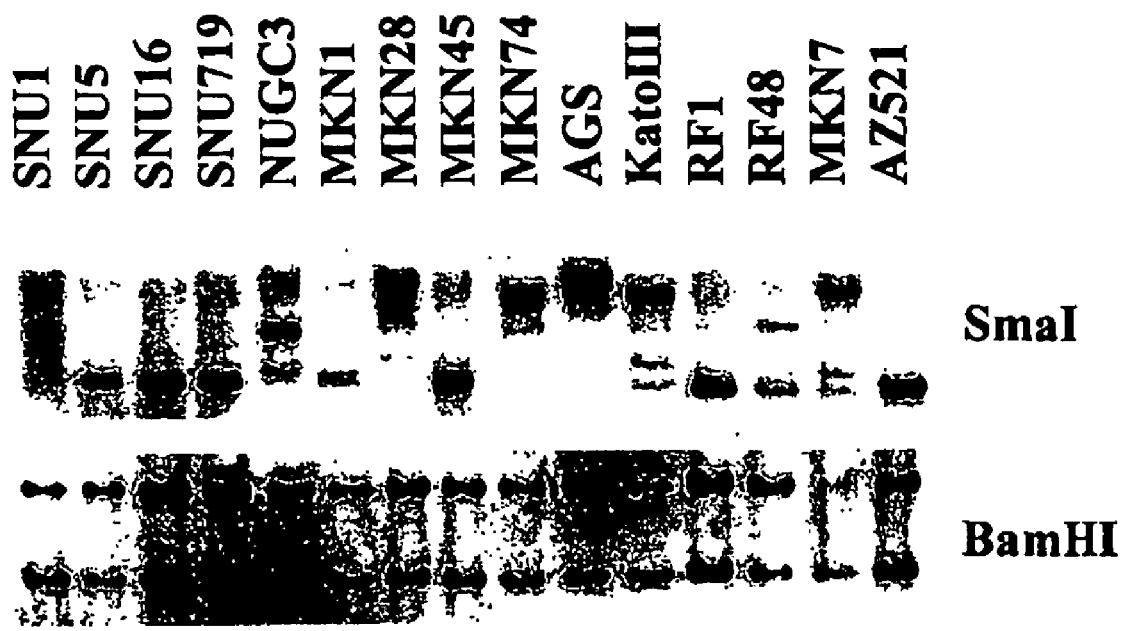
FIG. 7a is an autoradiogram resulting from Southern blotting analysis for DNA methylation in the vicinity of RUNX3 exon 1 in various gastric cancer cell lines by use of DNA probes which can detect parts of the CpG islands. The genomic DNAs were isolated from the cancer cell lines and treated with SmaI (upper), which can not digest methylated DNA, and BamHI (lower), which can digest DNA irrespective of DNA methylation.
Figure 7B:
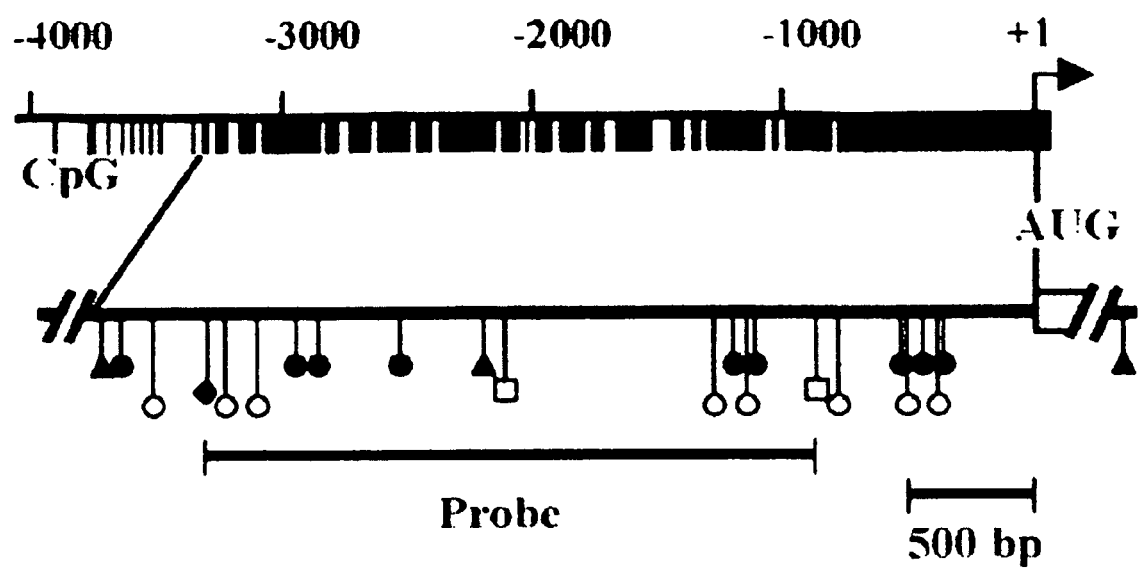
FIG. 7b is a schematic illustration showing restriction enzyme sites in the vicinity of RUNX3 exon 1 and the CpG frequency within typical CpG islands, with tick bars denoting the position of a DNA fragment used as a probe in genomic Southern blot analysis.

The SmaI digestion was observed to be greatly reduced specifically in those gastric cancer cell lines whose RUNX3 gene expression was not detected, that is, in the SNU1, NUGC3, MKN28, MKN74, AGS, and KatoIII cell lines, as shown in FIG. 7a. The MKN7 cell line in which the expression level was significantly low showed a partially methylated pattern (FIG. 7a). These results indicate that the expression of the RUNX3 gene is closely correlated with the level of DNA methylation at loci near RUNX3 exon 1 in cancer cell lines. Since RUNX3 gene-specific bands are detected in all of the cell lines despite differences in methylation, it can be concluded that some cancer cell lines in which the expression of the RUNX3 gene is not detected under normal conditions have the normal RUNX3 gene, but do not express it due to abnormal methylation.

5-2 Reactivation of the RUNX3 Gene

To determine whether the DNA methylation observed in Example 5-1 is the direct cause of the inactivation of the RUNX3 gene, the influence of a DNA methyltransferase inhibitor and a histone deacetylase inhibitor on the reactivation of the RUNX3 gene expression was analyzed.

The NUGC3, MKN28, and MKN74 cell lines (selected randomly from the cell lines showing no RUNX3 gene expression by RT-PCR analysis) were treated with 5-aza-3-deoxycytidine (AZA, 300 nM), which inhibits DNA methyltransferase, and trichostatin A (TSA, 1 mM), which inhibits histone deacetylase, alone or in combination. After 3 days of the treatment, total RNA was isolated from each cell line in accordance with the same standardized single-step guanidium method used in Example 4-1, and then analyzed for the expression of the RUNX3 gene by RT-PCR using the PS-N primer pair of SEQ. ID. NOS: 4 and 5.

Figure 8:
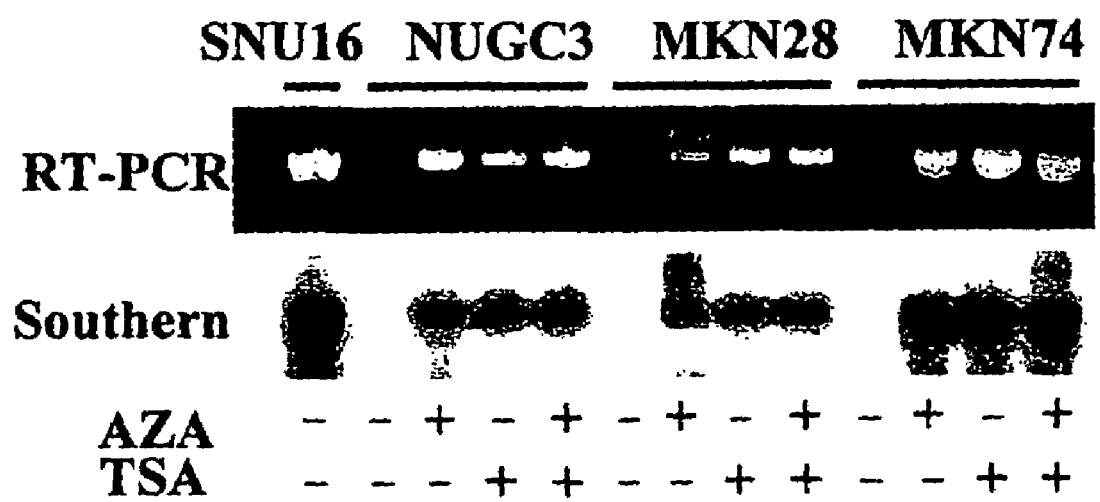
FIG. 8 shows the results of electrophoresis of RT-PCR products obtained from total RNAs of NUGC3, MKN28, and MKN74 after treatment with 5-aza-2-deoxycytidine (AZA, 300 nM) or trichostatin A (TSA, 1 mM), separately or in combination. The results indicate that the treatment with the DNA methyltransferase inhibitors or HDAC inhibitors allows the RUNX3 gene to be expressed.

Upon treatment with the DNA methyltransferase inhibitor or the histone deacetylase inhibitor, the expression of the RUNX3 gene was observed, as seen in FIG. 8. These results reveal that hyper-methylation suppresses the expression of the RUNX3 gene in about 37% of the gastric and lung cancer cells owing to the hyper-methylation of CpG islands at loci near the exon 1 of the RUNX3 gene.

The expression plasmid capable of expressing the sense RUNX3 gene, constructed in Example 1-1, was assayed for acute toxicity as follows.

Example 6

Acute Toxicity Test upon Parenteral Administration of pEF-BOS-Rx3 to Rat

An acute toxicity test was conducted using rats of a specific pathogen-free SD lineage at 6 weeks of age. pEF-BOS-Rx3 (prepared as described in Example 1-1) was suspended in 1 ml of a physiological saline solution and administered to the anterior tibialis of two rats at a dose of 1 mg/kg by intramuscular injection. After the injection, the rats were observed for death, clinical traits, and body weight changes, and serological and serobiochemical analyses were conducted. In addition, the rats were sacrificed in order to observe the abdominal and thoracic organs. In neither animal were specifically noteworthy clinical traits found. No animals died from the administration of the test material, and no changes were observed in the body weight. The serological assay, serobiochemical assay, and autopsy test were all normal. Accordingly, pEF-BOS-Rx3 was identified as safe, with an $LD_{50}$ of at least 1 mg/kg upon parenteral injection.

INDUSTRIAL APPLICABILITY

As described previously herein, the RUNX3 gene of the present invention shows excellent tumor suppressor activity and is indispensably involved in TGF-β-dependent programmed cell death (apoptosis). Additionally, the suppression of RUNX3 gene expression is attributed to abnormal DNA methylation of CpG islands located near exon 1 of the RUNX3 gene. Accordingly, the RUNX3 gene and its products (RNA and proteins) can be utilized for the development of gene therapy for cancers. Measurement of the abnormal DNA methylation in the vicinity of exon 1 of the RUNX3 gene is useful for diagnosis of cancers. In addition, chemicals capable of regulating the abnormal DNA methylation and its consequences (for examples DNA methyltransferase inhibitors and HDAC inhibitors) can be used as anticancer agents because of their ability to promote the expression of the RUNX3 gene.

What is claimed is:

1. A method for diagnosing cancers caused by a loss of RUNX3 expression due to the methylation of the nucleotide sequence of SEQ. ID. NO: 3, characterized by detecting the methylation of a nucleotide sequence SEQ. ID. NO: 3, containing CpG islands present near exon 1 of the RUNX3 gene, comprising the steps of:
   isolating genomic DNA from a tumor tissue of a subject;
   digesting the genomic DNA with a restriction enzyme sensitive to DNA methylation;
   separating the genomic DNA digests on an agarose gel by electrophoresis and transferring them onto a membrane;
   hybridizing the genomic DNA digests with a radiolabeled DNA probe for a RUNX3 gene; and
   exposing the membrane to a film and detecting the methylation of the nucleotide sequence of SEQ. ID. No: 3, whereby the detection of methylation indicates a cancer caused by a loss of RUNX3 expression.

2. A method for diagnosing cancers caused by a loss of RUNX3 expression due to the methylation of the nucleotide sequence of SEQ. ID. NO: 3, characterized by detecting the methylation of a nucleotide sequence SEQ. ID. NO: 3, containing CpG islands present near exon 1 of the RUNX3 gene, comprising the steps of:
   isolating genomic DNA from the blood or tumor tissue of a subject;
   digesting the genomic DNA with a restriction enzyme sensitive to DNA methylation;
   performing a polymerase chain reaction (PCR) with the genomic DNA digests serving as templates and with parts of the nucleotide sequence of SEQ. ID. NO: 3 serving as primers;
   separating the PCR products on an agarose gel by electrophoresis and detecting the amplification of a DNA sequence of interest, whereby the detection of amplification indicates a cancer caused by a loss of RUNX3 expression.

3. A method for diagnosing cancer caused by a loss of RUNX3 expression due to the methylation of the nucleotide sequence of SEQ. ID. NO: 3 comprising:
   detecting methylation of a nucleotide sequence containing CpG islands present near exon 1 of the RUNX3 gene, which is isolated from a subject.

4. The method of claim 3, wherein the nucleotide sequence containing CpG islands comprises SEQ. ID. NO: 3.

5. The method of claim 1, wherein the cancer is gastric cancer or lung cancer.

6. The method of claim 2, wherein the cancer is gastric cancer or lung cancer.

7. The method of claim 3, wherein the cancer is gastric cancer or lung cancer.

* * * * *